(12) United States Patent
Beitz et al.

(10) Patent No.: US 6,248,097 B1
(45) Date of Patent: *Jun. 19, 2001

(54) ABSORBENT ARTICLE WITH MORE CONFORMABLE ELASTICS

(75) Inventors: Mark John Beitz; Monica Lynn Bontrager, both of Appleton; Barbara Ann Gossen, Oshkosh; Chris Lee Heikkinen, Menasha; Daniel Hoo, Appleton; David Andrae Justmann, Hortonville; Richard Francis Keller, Fremont; Cynthia Helen Nordness, Oshkosh; Douglas Paul Rammer, Appleton; Lorry Francis Sallee, Pine River; Raymond Gerard St. Louis, Fremont; David James VanEperen, Appleton; Cynthia Louise Wyngaard, Kaukauna; Sandra Marie Yarbrough, Menasha; Roxanne Marie Zuleger, Appleton, all of WI (US); Steven Scott Friderich, Alpharetta, GA (US); Eric Scott Kepner, Fletcher, NC (US); Kuo-Shu Edward Chang, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/327,368

(22) Filed: Jun. 4, 1999

Related U.S. Application Data

(60) Provisional application No. 60/095,499, filed on Aug. 6, 1998.

(51) Int. Cl.[7] .............................. A61F 13/15; A61F 13/20
(52) U.S. Cl. ................................ 604/385.27; 604/385.01; 604/385.28; 604/358
(58) Field of Search ...................................... 604/358, 378, 604/385.01, 385.101, 385.25, 385.27

(56) References Cited

U.S. PATENT DOCUMENTS

| 3,901,236 | 8/1975 | Assarsson et al. . |
|---|---|---|
| 4,076,663 | 2/1978 | Masuda et al. . |

(List continued on next page.)

FOREIGN PATENT DOCUMENTS

| 0 217 032 A2 | 4/1987 | (EP) . |
|---|---|---|
| 0 532 002 B1 | 3/1993 | (EP) . |

(List continued on next page.)

OTHER PUBLICATIONS

Federal Test Method Standard (FTMS) No. 191A, Method 5514, "Water Resistance of Cloth; Low Range, Hydrostatic Pressure Method," Jul. 20, 1978, 3 pages.

(List continued on next page.)

*Primary Examiner*—John G. Weiss
*Assistant Examiner*—Michele Kidwell
(74) *Attorney, Agent, or Firm*—Paul Yee

(57) ABSTRACT

An absorbent article (10) which includes a backsheet layer (30) having a pair of laterally opposed and longitudinally extending side margins (20). Each side margin has an outwardly concave, terminal side edge contour 15 located at appointed leg opening regions (17) in an intermediate portion (16) of the side margin. Each concave side edge contour (15) has a selected longitudinal extent along a length dimension (26) of the article (10). A liquid permeable topsheet layer (28) is connected in a superposed facing relation to the backsheet layer (30), and an absorbent body (32) is sandwiched between the topsheet layer (28) and the backsheet layer (30). A separately provided gusset-flap composite member (19) is connected to at least one of the backsheet and topsheet layers along each of the leg opening regions (17). The gusset-flap member (19) provides a leg gusset section (142) and a containment flap section (144), and is distinctively configured to provide improved leakage resistance, fit and comfort.

25 Claims, 14 Drawing Sheets

U.S. PATENT DOCUMENTS

| | | |
|---|---|---|
| 4,286,082 | 8/1981 | Tsubakimoto et al. . |
| 4,585,448 | 4/1986 | Enloe . |
| 4,610,678 | 9/1986 | Weisman et al. . |
| 4,663,220 | 5/1987 | Wisneski et al. . |
| 4,699,823 | 10/1987 | Kellenberger et al. . |
| 4,704,116 | 11/1987 | Enloe . |
| 5,028,224 | 7/1991 | Pieper et al. . |
| 5,226,992 | 7/1993 | Morman . |
| 5,340,648 | 8/1994 | Rollins et al. . |
| 5,399,219 | 3/1995 | Roessler et al. . |
| 5,486,166 | 1/1996 | Bishop et al. . |
| 5,490,846 | 2/1996 | Ellis et al. . |
| 5,501,756 | 3/1996 | Rollins et al. . |
| 5,507,909 | 4/1996 | Rollins et al. . |
| 5,540,796 | 7/1996 | Fries . |
| 5,549,592 | 8/1996 | Fries et al. . |
| 5,562,650 | 10/1996 | Everett et al. . |
| 5,595,618 | 1/1997 | Fries et al. . |
| 5,605,735 | 2/1997 | Zehner et al. . |
| 5,820,973 | 10/1998 | Dodge, II et al. . |
| 5,827,259 | 10/1998 | Laux et al. . |
| 5,882,573 | 3/1999 | Kwok et al. . |
| 5,902,540 | 5/1999 | Kwok . |
| 5,904,298 | 5/1999 | Kwok et al. . |
| 5,904,675 | 5/1999 | Laux et al. . |
| 5,993,433 | 11/1999 | St. Louis et al. . |
| 6,077,375 | 6/2000 | Kwok . |
| B1 3,860,003 | 6/1990 | Buell . |
| B1 4,842,666 | 10/1992 | Werenicz . |
| B1 5,147,343 | 3/1998 | Kellenberger . |

FOREIGN PATENT DOCUMENTS

| | | |
|---|---|---|
| WO 94/18927 A1 | 9/1994 | (WO) . |
| WO 95/16425 A2 | 6/1995 | (WO) . |
| WO 96/05792 A1 | 2/1996 | (WO) . |
| WO 96/32084 A1 | 10/1996 | (WO) . |
| WO 97/18346 A1 | 5/1997 | (WO) . |
| WO 97/20532 A1 | 6/1997 | (WO) . |
| WO 99/20215 A1 | 4/1999 | (WO) . |

OTHER PUBLICATIONS

TAPPI Official Test Method T 543 om–94, "Bending Resistance of Paper (Gurley Type Tester)," published by the TAPPI Press, Atlanta, Georgia, pp. 1–7.

ABSORBENT ARTICLE WITH MORE CONFORMABLE ELASTICS

This application claims benefit of provisional application Ser. No. 60/095,499 filed Aug. 6, 1998.

FIELD OF THE INVENTION

The present invention relates to an article having one or more elasticized, peripheral margins. More particularly, the invention relates to an article which incorporates a distinctively elasticized containment system at legband and/or waistband portions of the article, has a distinctively proportioned shape.

BACKGROUND OF THE INVENTION

Conventional absorbent articles, such as disposable diapers, have been constructed with various types of elasticized waistbands and elasticized leg bands or leg cuffs. Such article designs have also included additional, elasticized containment or barrier flaps at the leg and/or waist sections of the article. Particular article designs have incorporated a stretchable outer cover composed of an elastomeric web material, such as a stretch-bonded laminate which includes a layer of nonwoven fabric. Other conventional designs have included separate elastomeric or nonelastomeric side panel members connected to the lateral side edges of a backsheet or outercover member, and have included fastening systems and fastening tabs connected to the side panels for securing the article on a wearer. The absorbent articles have included various shapes, such as rectangular, hour-glass, T-shape and I-shape. The absorbent pads of the articles have also incorporated these shapes.

Articles which incorporate conventional elasticized margins and conventional barrier flap configurations at their legband sections have, however, exhibited various shortcomings. For example, it has been difficult to avoid red marking of the wearer's skin and difficult to maintain the desired operation of the barrier flaps when the articles are being worn. Even when the barrier flaps are constructed of an elastomeric material or otherwise elasticized, it has been difficult to maintain contact between the movable edge of the barrier flap and the wearer's body and has been difficult to reliably hold the flap open for an effective receipt and containment of urine and feces. It has also been difficult to provide a trim, un-bunched fit of the article in the crotch region between the wearer's legs. In addition, it has been difficult to maintain a close fit of the elasticized leg cuffs about the wearer's legs during the movements of the wearer while also providing a neat and tailored appearance of the absorbent article. It has also been difficult to place the article on the wearer due to the article width in its crotch region. As a result, there has been a continued need for improved containment structures at the various regions of the absorbent articles.

BRIEF DESCRIPTION OF THE INVENTION

The present invention can provide a distinctive article having a longitudinal direction and a lateral cross-direction. The article includes a backsheet layer having a pair of laterally opposed side margins, with each side margin having a terminal side edge contour located at an appointed leg opening region in each of the side margins. A substantially liquid permeable topsheet layer is connected in superposed relation to the backsheet layer, and an absorbent body is positioned and held between the topsheet layer and the backsheet layer. A separate, elasticized gusset-flap member is connected to the article along each of the appointed leg opening regions, and each gusset-flap member has a leg gusset section and a containment flap section. The leg gusset section is configured to extend beyond and bridge between opposed, spaced-apart portions of an associated one of the side edge contours of the backsheet layer.

In particular aspects, the article of the invention can include a backsheet layer having a pair of laterally opposed and longitudinally extending side margins, with each side margin having an outwardly concave, terminal side edge contour located at appointed leg opening regions in an intermediate portion of the side margin. Each concave side edge contour has a selected longitudinal extent along a length dimension of the article. A substantially liquid permeable topsheet layer is connected in a superposed facing relation to the backsheet layer, and an absorbent body is sandwiched between the topsheet layer and the backsheet layer. A separately provided gusset-flap composite member is connected to at least one of the backsheet and topsheet layers along each of the leg opening regions, and the gusset-flap member provides a leg gusset section and a containment flap section. A gusset-flap attachment has a longitudinal extent and secures each gusset-flap member to the article, and an additional perimeter bond attachment is positioned adjacent to and laterally outboard from each gusset-flap attachment. Each perimeter bond attachment is configured to secure its associated leg gusset section to the article beside its corresponding, outwardly concave terminal side edge contour of the article along at least a partial length of the terminal side edge contour, and the perimeter bond attachment extends inboard from a terminal side edge of the backsheet layer adjacent an article juncture region. The article juncture region is where an overlapping portion of an outboard edge of at least one leg gusset section intersects across the terminal side edge contour of the backsheet layer, and where the overlapping portion of the outboard edge of the at least one leg gusset section is superposed over a bodyside surface of the backsheet layer.

In another aspect, the article of the invention can include an end portion of a first arrangement of elastomeric members in the leg gusset section which is substantially deactivated to provide at least one gusset end portion of each leg gusset section which is substantially non-gathered along the longitudinal direction. Additionally, a leg gusset, outboard securement can attach at least one gusset end portion of each leg gusset section to the article.

In a further aspect, the article of the invention can include an end portion of a second arrangement of at least one elastomeric member in the containment flap section which is substantially deactivated to provide at least one flap end portion of each containment flap section which is substantially non-gathered along the longitudinal direction. Additionally containment flap, distal securement array can attach at least one flap end portion of each containment flap section to the article.

In yet another aspect, the article of the invention can include a distinctively configured backsheet layer. The backsheet layer can have a maximum waistband width_A along said cross dimension, and a minimum crotch width_B at an intermediate portion of said backsheet layer. A quotient of the maximum waistband width_A divided by the minimum crotch width_B of said backsheet layer is at least a predetermined value, such as a minimum value of about 1.6. The backsheet layer can also have a length_K along which a cross-directional width of the backsheet is not more than a value_C, where the value_C is determined by the formula, $$(\text{value\_C}) = (0.8)*(\text{width\_B}) + (0.2)*(\text{width\_A}).$$

Additionally, the length_K can be at least about 30% of an overall length of said article, and the backsheet layer can have a front turn-out angle_θ which is within a selected range, such as a range of about 115–135 degrees.

In still a further aspect, the article of the invention can include a distinctively configured absorbent retention portion. The backsheet layer can have a maximum waistband width_A along the cross dimension of the article, and the absorbent retention portion can have a minimum width_P along the cross dimension at an intermediate portion of the retention portion. A quotient of the width_A divided by said width_P is at least a predetermined value, such as a minimum value of about 3.3. The absorbent retention portion can also have a longitudinal length_Z along which a cross-directional width of the retention portion is not more than a value_Q, where the value_Q is determined by the formula, $$(value\_Q)=(0.8)*(width\_P)+(0.2)*(width\_A).$$

Additionally, the length_Z can be at least about 30% of an overall length of said article.

The configurations and arrangements of the various aspects of the invention can provide an article having a gentle, soft, and more conformable leg gather, and can provide a barrier flap structure that can more reliably and more effectively maintain an open position when the associated absorbent article is being worn. In addition, the open flap configuration can be sustained while avoiding excessive irritation of the wearer's skin. The resultant article can exhibit less gapping at the leg opening regions, and can provide a more cushioning operation and appearance. The article can also be more easily placed onto the wearer. Additionally, the article can provide a leg gather which may move more independently from the main portion of the absorbent article to provide a leg gather more conformable to the leg. The article can also provide leg gusset and containment flap configurations which provide a more tortuous path for better resistance against the leakage of any free liquids in the absorbent article. The arrangements of the constituent components and the combination of operational parameters, such as the controlled stiffness and the controlled articulation of the barrier flap, can advantageously provide an improved absorbent structure which can have less leakage, and can afford increased comfort to the wearer.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The present invention will be described herein in relationship to producing an elasticized containment system for absorbent articles, particularly disposable absorbent articles. The articles can be placed against or in proximity to the body of a wearer to absorb and contain various exudates discharged from the body, and are intended to be discarded after a limited period of use. The articles are not intended to be laundered or otherwise restored for re-use. While the present description will particularly be made in the context of a diaper article, it should be understood that the present invention is also applicable to other articles, such as caps, gowns, drapes, covers, adult incontinence garments, sanitary napkins, children's training pants, and the like.

In addition, the invention will be described in the context of its various configurations and aspects. It should be appreciated that alternative arrangements of the invention can comprise any combination which includes one or more of the various configurations and aspects of the invention.

Figure 1:
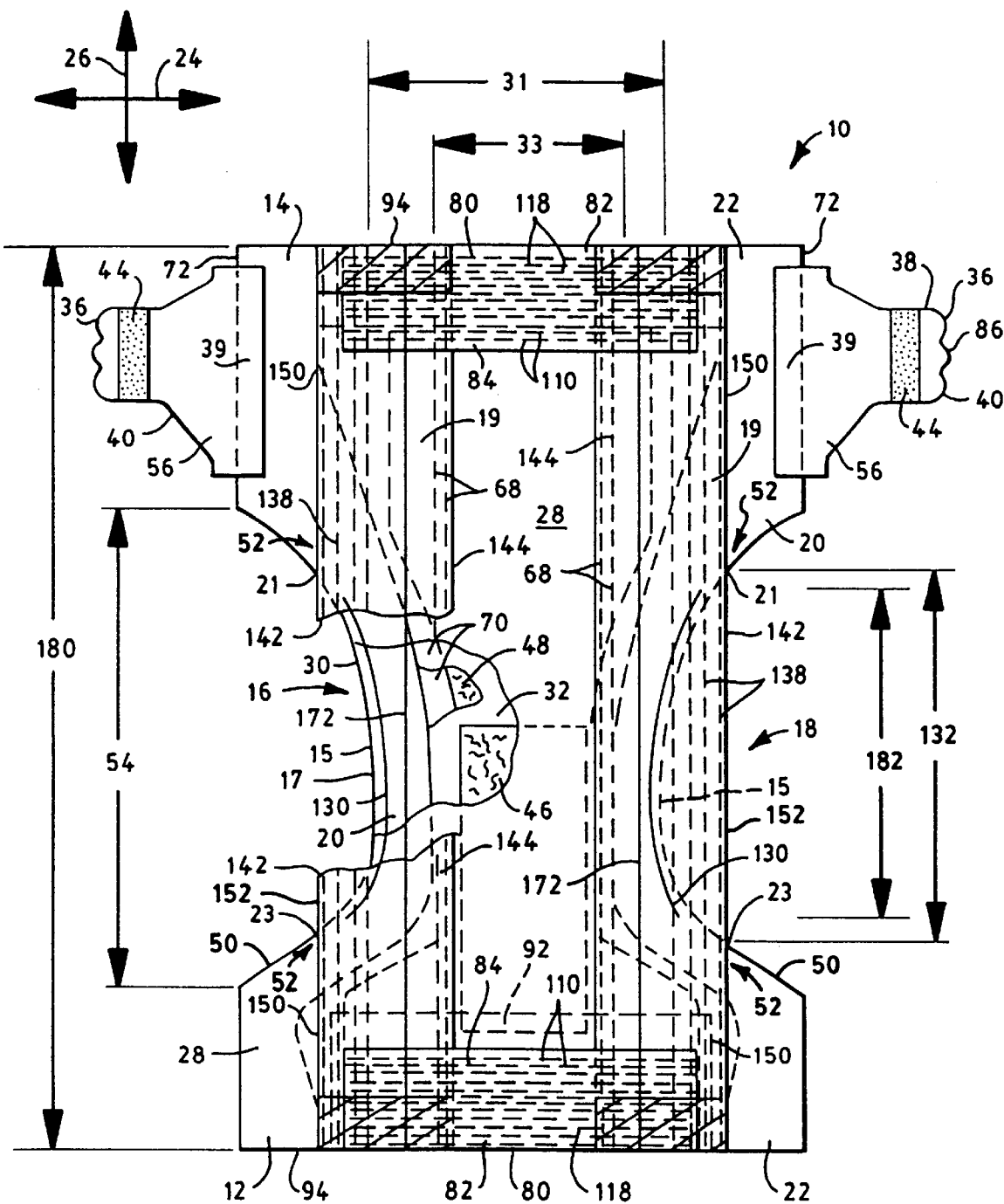
FIG. 1 representatively shows a partially cut-away, top plan view of an article of the invention.
Figure 2:
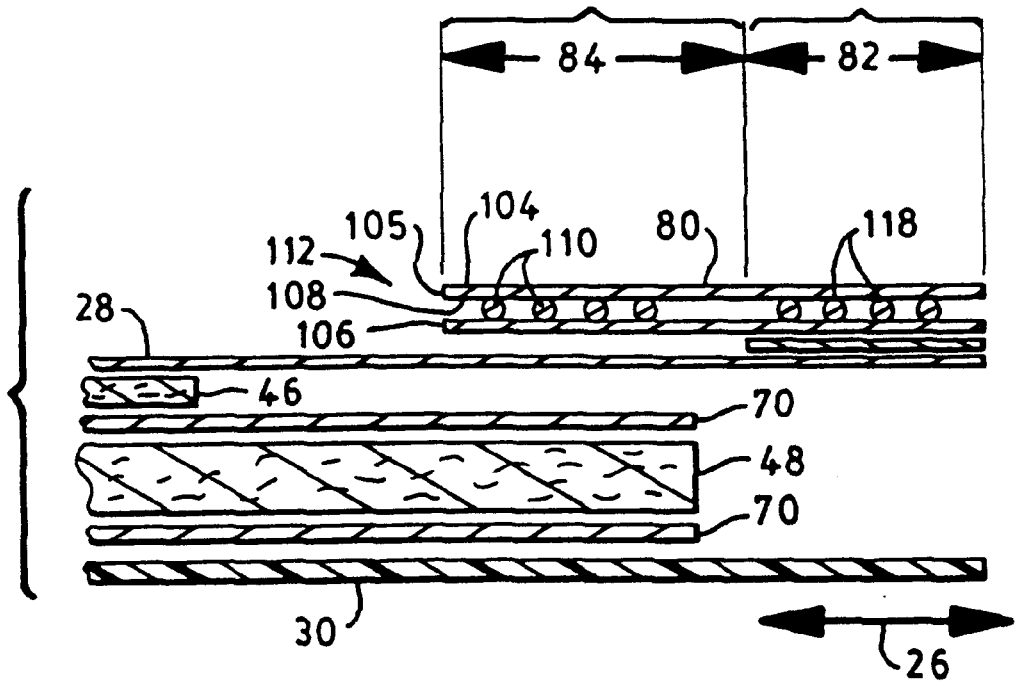
FIG. 2 representatively shows a schematic, expanded cross-sectional view of the waist elastic system and the waist, barrier flap system of the invention taken along a longitudinal centerline of the article when the flap or pocket section is in its flat-out, uncontracted condition.
Figure 3:
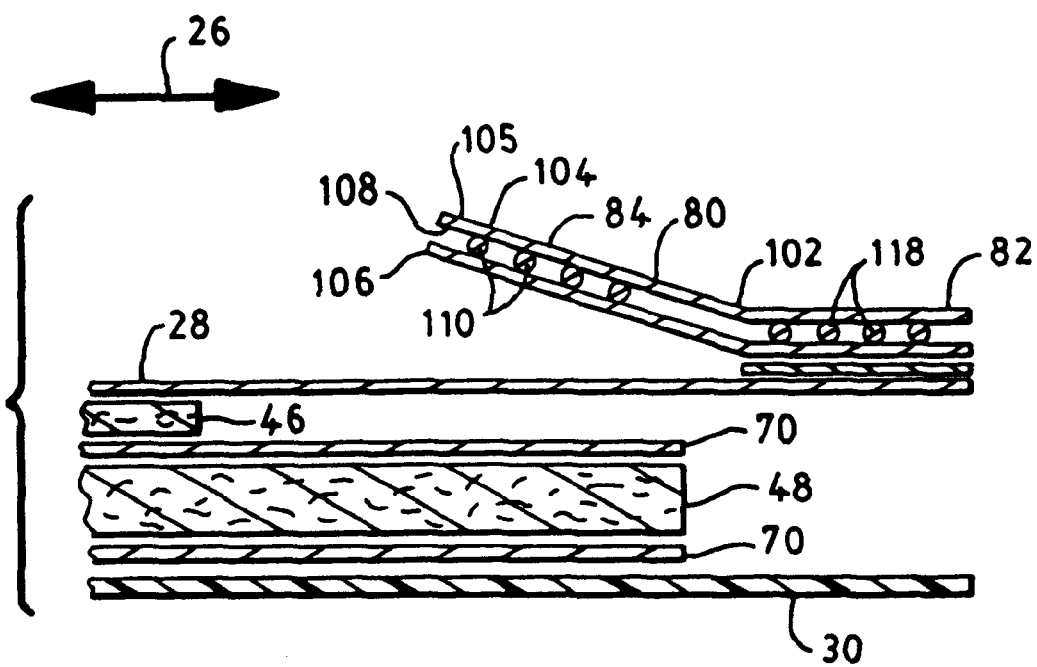
FIG. 3 representatively shows a schematic, expanded cross-sectional view of the waist elastic system and the waist, barrier flap system of the invention taken when the flap or pocket section is in its contracted and opened condition.

With reference to FIGS. 1, 2, and 3, a representative article, such as a diaper 10, has a lateral cross-dimension or cross-direction 24, and a length-wise longitudinal dimension or longitudinal direction 26. The article includes a front waistband portion 12, a back waistband portion 14, an intermediate portion 16 which interconnects the front and back waistband portions, and a pair of laterally opposed side margins 20. Extending along the side margins 20 are separately provided, integrally assembled gusset-flap members 19 which include a containment flap section 144 and a leg gusset section 142. The containment flap section 144 and/or leg gusset section 142 can be liquid permeable, or can be operably resistant to the passage of liquid therethrough during ordinary conditions of use. In desired arrangements, the containment flap section and/or leg gusset section can be substantially liquid impermeable. The article has a backsheet layer 30, a liquid permeable topsheet layer 28 connected in superposed relation to the backsheet layer, and an absorbent body structure 32 sandwiched between the topsheet layer and the backsheet layer. An elastomeric component, such as an elasticized, waist pocket member 80, may optionally be connected to at least one of the backsheet and topsheet layers along at least one end margin 22 of the article.

The representatively shown article includes a pair of longitudinally opposed end margins 22, and a pair of laterally opposed elasticized side margins 20. The elasticized, waist pocket member 80 is connected and attached to at least one of the backsheet and topsheet layers along at least one end margin 22 of the article. The shown waist pocket member 80 includes an extending flange section 82 and an extending pocket section 84. The pocket section 84 of the waist pocket/flap member 80 includes a substantially fixed edge portion 102 secured to the article, and includes an elasticized, gathered moveable edge portion 104 which is longitudinally spaced from the fixed edge portion 102. The pocket section also includes a substantially liquid impermeable pocket barrier layer 106, and a pocket fabric layer 108 connected in a laminated, facing relation with the pocket barrier layer. A plurality of separate, laterally extending pocket elastic members 110 are sandwiched between the pocket barrier layer 106 and the pocket fabric layer 108 to provide an elasticized waist pocket composite 112 which is substantially laterally gathered.

A fastening system 40 is operably connected and joined to the article at either or both of the laterally opposed end regions 72 of at least one of the front and rear waistband sections, such as the illustrated rear waistband 14. A cooperating side panel member 56 can be associated with each fastening system and may be constructed to be nonelasticized, or may be constructed to be elastomerically stretchable at least along the laterally extending cross-dimension 24 of the article. In addition, a fastening tab 36 can be attached to extend laterally outboard from each side panel member 56.

Figure 4:
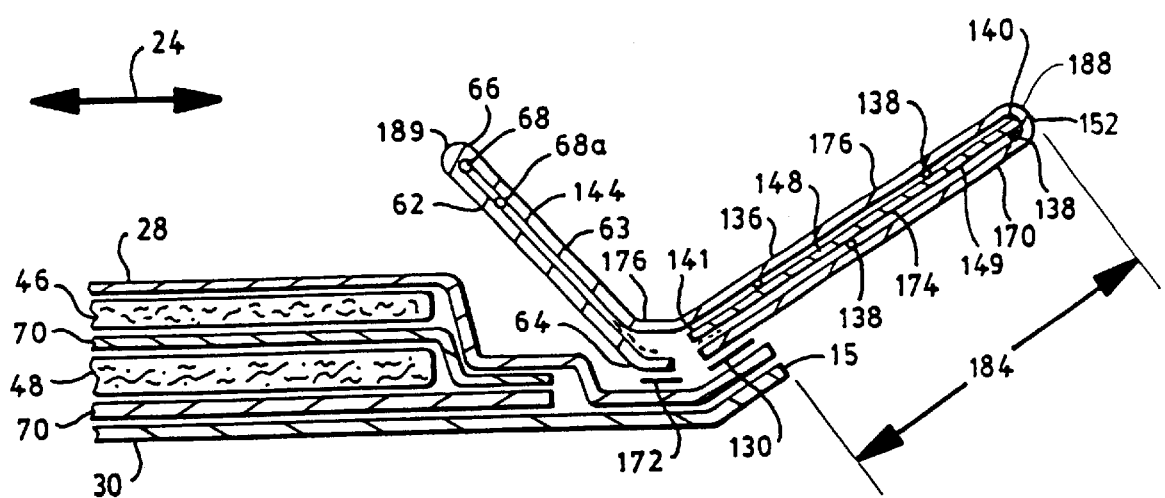
FIG. 4 representatively shows a schematic, expanded, lateral cross-sectional view of one of the gusset-flap members taken through the crotch section of the article.
Figure 5:
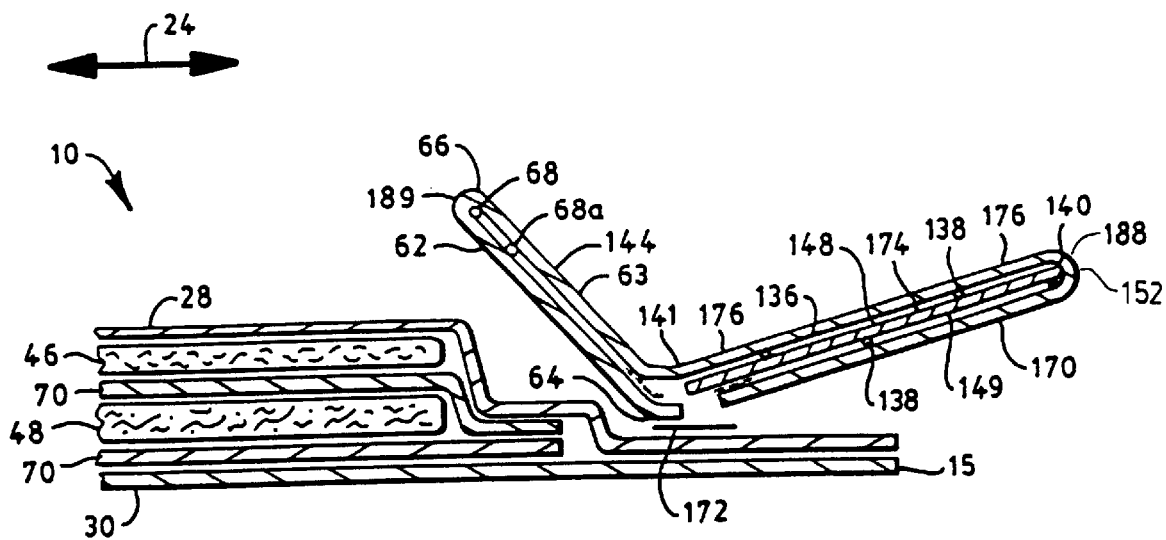
FIG. 5 representatively shows a schematic, expanded, lateral cross-sectional view of one of the gusset-flap members and its adjacent containment flap section, taken through another section of the article.

With reference to FIGS. 1 and 4, particular configurations of the invention can include a backsheet layer 30 having a pair of laterally opposed and longitudinally extending side margins 20. Each side margin has an outwardly concave, terminal side edge contour 15 located at appointed leg opening regions 17 in an intermediate portion 16 of each of the side margins. Each concave side edge contour 15 has a selected longitudinal extent 54 along the longitudinal, length dimension 26 of the article 10. The porous, liquid permeable topsheet layer 28 has a laterally extending width and a longitudinally extending length, and is connected in superposed relation to the backsheet layer 30. The absorbent body structure 32, is sandwiched and operably secured between the backsheet layer 30 and the topsheet layer 28. The separately provided gusset-flap composite member 19 is connected to at least one of the backsheet and topsheet layers along each of the leg opening regions 17. The gusset-flap member 19 provides a leg gusset section 142 and a containment flap section 144. Each leg gusset section 142 is configured to extend beyond and bridge across its corresponding, outwardly concave terminal side edge contour 15 of the backsheet layer 30, and is configured to provide an elasticized and gathered leg opening at the side margin of the article. Each containment flap section 144 is integrally formed with a corresponding one of the leg gusset sections 142 and is positioned relatively inboard therefrom to provide the gusset-flap member 19. Each containment flap section 144 has a substantially fixed edge 64 located proximally adjacent to a one of the elasticized side margins 20, and has a elasticized and gathered, distal, movable edge portion 66. In the various configurations of the invention, a gusset flap attachment 172 secures each gusset-flap 19 to the article. Each gusset-flap attachment 172 can have a predetermined longitudinal extent, and can, for example, secure its corresponding gusset-flap member to the article along a fixed edge portion 64 of each containment flap section 144.

In particular aspects, the each said gusset-flap member 19 can include a barrier layer 174 having a pair of laterally opposed, longitudinally extending, barrier layer side edges, and first and second major facing surfaces. Desirably, the barrier layer can be substantially liquid impermeable. A fabric layer 176 is joined in facing relation with the first facing surface of said barrier layer, and the fabric layer has a leg gusset region and a containment flap region. In desired arrangements, the fabric layer may also have an outboard side portion 170 and an inboard side portion 62. The outboard side portion can be arranged to wrap around at least one side edge of said barrier layer and extend inboard therefrom along said second facing surface of said barrier layer. The first arrangement of the first plurality of separate, longitudinally extending elastomeric members 138 can be attached to and sandwiched by the barrier layer 174 and the fabric layer 176 within the leg gusset section 142 of the gusset-flap member. The second arrangement of at least one longitudinally extending elastomeric member 68 can be attached to at least the fabric layer within each containment flap section 144 of the gusset-flap member.

Articles having separately provided gusset-flap members 19 are described in U.S. patent application Ser. No. 560,525 which was filed Dec. 18, 1995 by D. R. Laux et al. and entitled AN ABSORBENT ARTICLE WITH IMPROVED ELASTIC MARGINS AND CONTAINMENT SYSTEM; and in U.S. patent application Ser. No. 954,400 which was filed Oct. 20, 1997 by R. St. Louis et al. and entitled ABSORBENT ARTICLE WITH ENHANCED ELASTIC DESIGN FOR IMPROVED AESTHETICS AND CONTAINMENT. The entire disclosures of these documents are incorporated herein by reference in a manner that is consistent with the present disclosure.

The gusset-flap member 19 can include the barrier layer 174 having a pair of laterally opposed, longitudinally extending barrier layer side edges 140 and 141, and having a first major facing surface 148 and a second major facing surface 149. The gusset-flap fabric layer 176 may be composed of a nonwoven fabric, and can be positioned and joined in an immediate, facing relation with the first facing surface 148 of the gusset-flap barrier layer 174. The fabric layer 176 includes a leg gusset region 136, an outboard side portion 170 of the leg gusset region, a containment flap region 63, and an inboard side portion 62 of the containment flap region. The outboard side portion 170 of the fabric layer 176 can be arranged to wrap around at least one side edge of the barrier layer 174 and to extend inboard therefrom along the second facing surface 149 of the barrier layer. Additionally, either or both of the longitudinally extending, terminal edge regions of the gusset flap fabric layer 176 may be attached to the remainder of the gusset-flap by one or more gusset-flap fabric edge securements 126. These fabric edge securements can be accomplished by various techniques known in the art, such as ultrasonic bonding, thermal bonding, embossing, adhesive bonding and the like, as well as combinations thereof.

A first arrangement of a first plurality of separate, longitudinally extending elastomeric members 138 can be attached and sandwiched by the barrier layer 174 and the fabric layer 176 within the leg gusset section 142 of the gusset flap member 19. A second arrangement of at least one longitudinally extending elastomeric member 68 can be attached to at least the fabric layer 176 within each containment flap section 144 of the gusset-flap member 19. The first and second arrangements of elastomeric members 138 and 68 can thereby provide an elastomeric, substantially longitudinally gathered, gusset-flap composite member 19.

The leg gusset section 142 of each gusset-flap 19 can be configured to extend beyond and past the concave side edge contours 15 of the backsheet layer 30 to provide an elasticized leg cuff in at least the intermediate portion of the article. Additionally, each gusset section 142 is configured to bridge between opposed, spaced-apart portions 21 and 23 of an associated one of the concave side edge contours 15 of the backsheet layer 30. In particular, each leg gusset section is configured to extend beyond and to bridge between opposed spaced-apart portions 21 and 23 to thereby. span across a "mouth" of a generally C-shaped gap formed by the terminal edge of its corresponding side edge contour 15. Each gusset-flap member 19 may be operably attached to the inward, bodyside surface of the topsheet 28.

The various configurations of the invention can include two or more cooperating gusset-flaps 19, such as the shown laterally opposed pair of gusset-flaps. With respect to each other, the gusset-flaps can be arranged to be parallel or non-parallel to each other, and each individual gusset-flap can be straight and/or curvilinear.

In particular configurations of the invention, the inboard side portion 62 of the gusset-flap fabric layer 176 is arranged to fold and wrap around an appointed folding line or other region. The resultant, folded over portion can then be arranged to operatively sandwich or otherwise enclose the second arrangement 68 of at least one longitudinally extending elastomeric member.

In other arrangements of the invention, the barrier layer 174 can be configured to extend into the containment flap section 144 of the gusset-flap 19, and the inboard side portion 62 of the gusset-flap fabric layer 176 can be arranged to wrap around the second side edge 141 of the barrier layer 174 to extend along the second major surface 149 of the barrier layer. In addition, the second set 68 of the at least one longitudinally extending elastomeric member can be attached between the containment flap region 63 of the fabric layer 176 and a containment flap region 61 of the barrier layer 174 within the containment flap section 144 of each gusset flap member 19.

Further aspects of the invention can provide an absorbent article in which the backsheet layer 30 may include a crotch region thereof having a crotch width which is particularly narrow. For example, the crotch width of the backsheet layer at its narrowest location can be not more than a maximum of about 240 mm, and desirably, may be not more than about 160 mm. Other aspects of the invention can provide an article in which the absorbent body 32 is constructed with a crotch width which is also quite narrow. For example, the crotch width of an absorbent retention portion at its narrowest location can be not more than a maximum of about 102 mm, and desirably, may be not more than about 76 mm. In still other aspects of the invention, each separately provided, elasticized and gathered gusset-flap 19 can be connected to at least one of the topsheet and backsheet layers with a gusset attachment 172 which extends along each of the appointed leg opening regions. Each gusset attachment 172 can be spaced from an associated, proximally adjacent, longitudinally extending side edge of the absorbent body 32 by a gusset spacing distance of not more than about 51 mm. Alternatively, the gusset spacing distance can be not more than about 25 mm, and optionally, can be not more than about 13 mm, at least when measured within the crotch region 18 of the article. The various aspects and configurations of the invention can provide distinctive combinations of softness, body conformity, reduced bunching between the wearer's legs, reduced red-marking of the wearer's skin, and improved leakage protection.

Each gusset-flap has a gusset-flap attachment 172 which extends longitudinally and secures each gusset-flap member to the article along a fixed edge portion of each containment flap section, and can have an additional perimeter bond attachment 130 which is positioned adjacent to and laterally outboard from its corresponding gusset-flap attachment 172. Each perimeter bond attachment 130 is configured to secure its associated leg gusset section 142 to the article beside its corresponding, outwardly concave terminal side edge contour 15 of the article, particularly the side edge contour of the backsheet layer, along at least a partial length of the terminal side edge contour. The perimeter bond attachment 130 extends inboard from a terminal side edge of the backsheet layer adjacent an article juncture region 52. The article juncture region is where an overlapping portion of an outboard edge 152 of the leg gusset section 142 intersects across the terminal side edge contour of the backsheet layer, and where the overlapping portion of the outboard edge 152 of the leg gusset section is superposed over a bodyside surface of the backsheet layer 30.

In another aspect of the invention, the article of the invention can include at least one end portion 137 of the first arrangement of elastomeric members 138 in the leg gusset section 142 which is substantially deactivated to provide at least one gusset end portion 150 of each leg gusset section 142 which is substantially non-gathered along the longitudinal direction 26. In particular arrangements, an outboard deadening array 158 (e.g., FIG. 16) can be employed to deactivate the end portion of the first arrangement of elastomeric members.

A leg gusset, outboard securement 160 may be employed to attach at least one gusset end portion 150 of each leg gusset section 142 to the article. Desirably, the outboard securement attaches the outboard side edge 152 of the leg gusset section to an appointed portion of the article, such as the article topsheet layer 28. Optionally, the outboard securement 160 may be configured to deactivate the at least one end portion 137 of the first arrangement of elastomeric members 138 in the leg gusset section 142 to provide the at least one gusset end portion 150 of each leg gusset section 142 which is substantially non-gathered.

In further aspects, at least one end portion 69 of the second arrangement of at least one elastomeric member 68 in the containment flap section 144 can be substantially deactivated to provide at least one flap end portion of each containment flap section which is substantially non-gathered along the longitudinal direction 26. In particular arrangements, a distal deadening array 78 can be employed to deactivate the end portion of the second arrangement of elastomeric members.

The article of the invention can include a containment flap, distal securement 79 which attaches at least one flap end portion 67 of each containment flap section 144 to the article. Desirably, the distal securement attaches the distal, movable edge 66 of the containment flap section to an appointed portion of the article, such as the topsheet layer 28. In particular configurations, the containment flap, distal securement 79 can also deactivate the at least one end portion 69 of the second arrangement of at least one elastomeric member 68 in the containment flap section 144 to provide the at least one flap end portion of each containment flap section which is substantially non-gathered.

Figure 12:
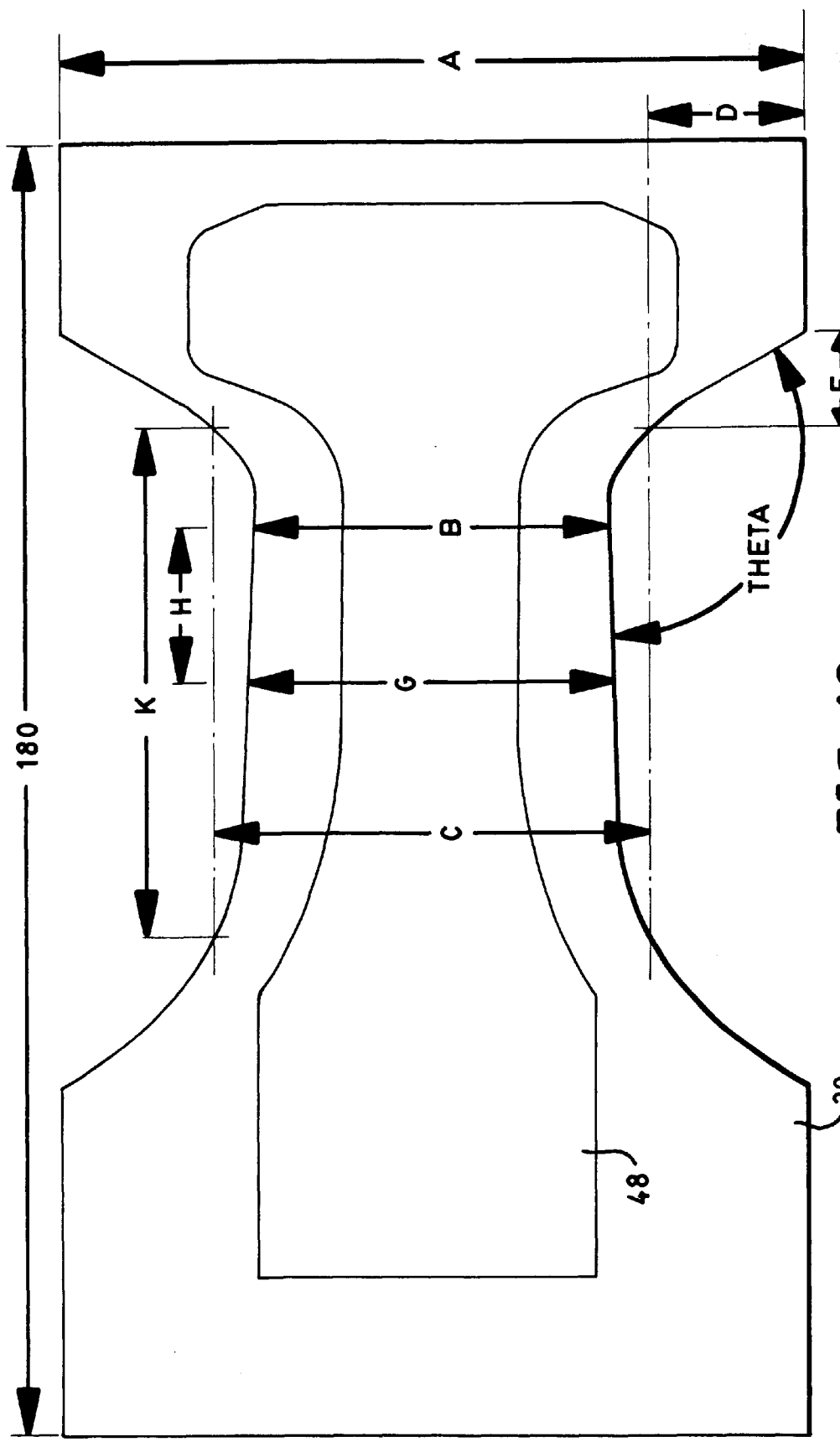
FIG. 12 representatively shows a schematic, top plan view which illustrates particular dimensions of the backsheet layer of the absorbent article.

Yet another aspect of the article of the invention can include a distinctively configured backsheet layer 30 (e.g. FIG. 12). The backsheet layer can have a maximum waistband width_A along the cross dimension 24, and a minimum crotch width_B at an intermediate portion of the backsheet layer. A quotient of the maximum waistband width_A divided by the minimum crotch width_B of the backsheet layer 30 is at least a predetermined value. The backsheet layer can also have a length_K along which a cross-directional width of the backsheet is not more than a value_C, where the value_C is determined by the formula, $$(value\_C)=(0.8)*(width_B)+(0.2)*(width_A).$$

The length_K can be at least a minimum percentage of the overall length 180 of the article. The backsheet layer 30 can also include a front turn-out angle_θ which is within a selected range, such as a range of about 115–135 degrees.

Figure 13:
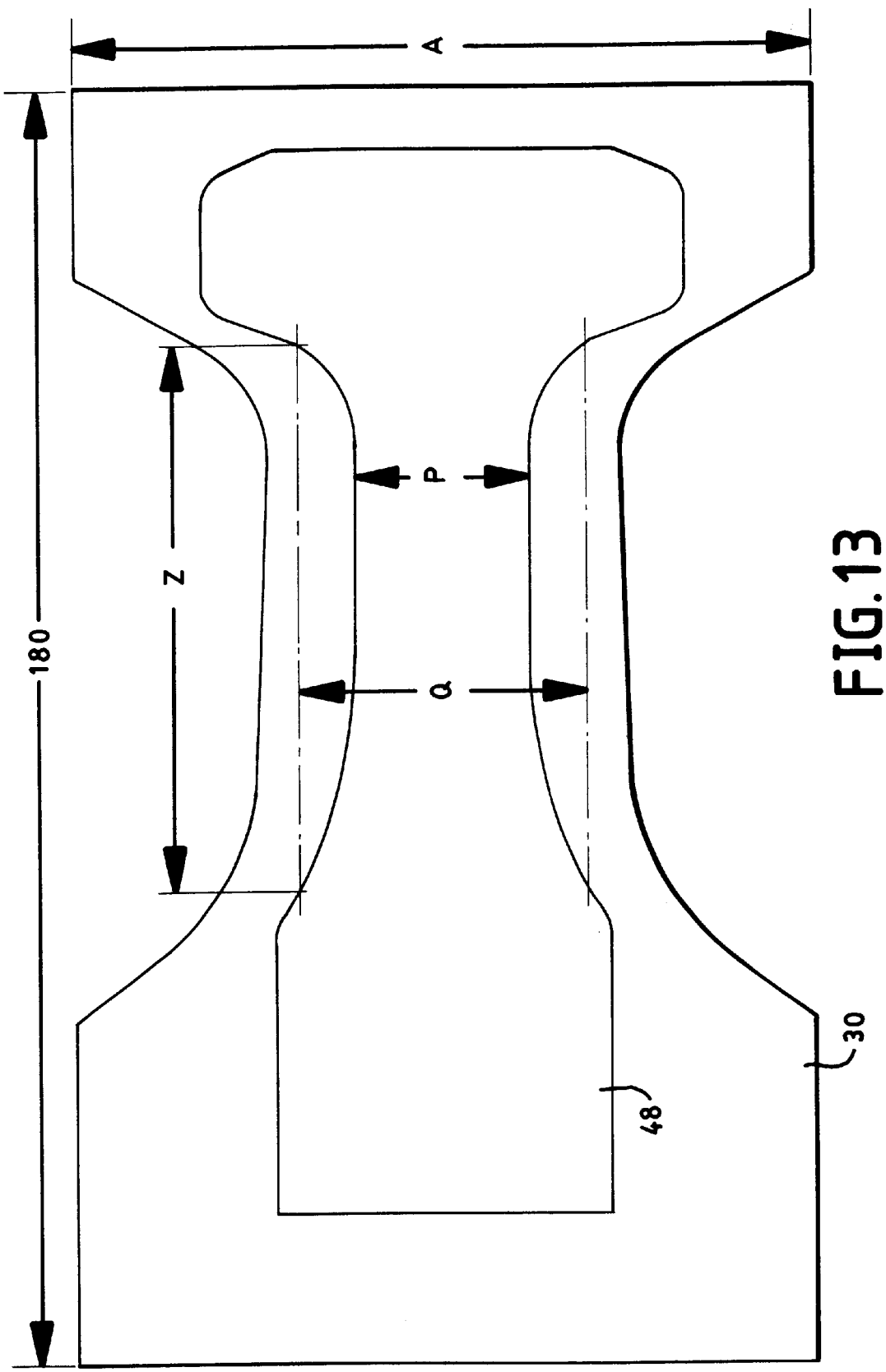
FIG. 13 representatively shows a schematic, top plan view which illustrates particular dimensions of the retention portion of the absorbent article.

A further aspect of the article of the invention can include a distinctively configured absorbent retention portion 48 (e.g. FIG. 13). The backsheet layer 30 can have a maximum waistband width_A along the cross dimension 24 of the article, and the absorbent retention portion 48 can have a minimum width_P along the cross dimension at an intermediate portion of the retention portion 48. A quotient of the width_A divided by the width_P is at least a predetermined value, such as a minimum value of at least about 3.3.

The absorbent retention portion can also have a longitudinal length_Z along which a cross-directional width of the retention portion is not more than a value_Q, where the value_Q is determined by the formula, $$(value\_Q)=(0.8)*(width\_P)+(0.2)*(width\_A).$$

The length_Z is at least a selected proportion of the overall length 180 of the article to provide improved fit and conformance.

FIG. 1 is a representative, top plan view of diaper 10 of the present invention in its flat-out, uncontracted state (i.e., with all elastic induced gathering and contraction removed). Portions of the structure are partially cut away to more clearly show the interior construction of diaper 10, and the surface of the diaper which contacts the wearer is facing the viewer. The outer edges of the diaper define a periphery in which the longitudinally extending side edge margins are designated 20 and the laterally extending end edge margins are designated 22. The side edges define leg openings for the diaper, and optionally, are curvilinear and contoured. The end edges are shown as straight, but optionally, may be curvilinear.

Diaper 10 typically includes a porous, liquid permeable topsheet 28; a substantially liquid impermeable backsheet 30; an absorbent structure 32, positioned and connected between the topsheet and backsheet; a surge management portion 46; and elastomeric members for elasticizing the diaper margins at the legband and waistband regions. The surge management portion is positioned in liquid communication with the absorbent structure, and the absorbent structure includes a retention portion 48. The topsheet 28, backsheet 30, absorbent structure 32, surge management portion 46 and the elastic members may be assembled in a variety of well-known diaper configurations. In addition, the diaper can include a system of relatively inboard barrier flaps, such as containment flap sections 144, positioned proximally adjacent to the diaper legbands.

As representatively shown, the topsheet 28 and backsheet 30 may be generally coextensive, and may have length and width dimensions which are generally larger than the corresponding dimensions of absorbent structure 32. Topsheet 28 is associated with and superimposed on backsheet 30, thereby defining the periphery of diaper 10. The waistband regions comprise those upper portions of diaper 10, which when worn, wholly or partially cover or encircle the waist or mid-lower torso of the wearer. The intermediate region 16 lies between and interconnects waistband regions 12 and 14, and includes a crotch region 18 which comprises that portion of diaper 10 which, when worn, is positioned between the legs of the wearer and covers the lower torso of the wearer. Thus, the crotch region 18 is an area where repeated fluid surges typically occur in the diaper or other disposable absorbent article.

The topsheet 28 presents a body-facing surface which is compliant, soft-feeling, and non-irritating to the wearer's skin. Further, the topsheet 28 can be less hydrophilic than retention portion 48, and is sufficiently porous to be liquid permeable, permitting liquid to penetrate through its thickness. A suitable topsheet 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 28 is typically employed to help isolate the wearer's skin from liquids held in absorbent structure 32. Various woven and nonwoven fabrics can be used for topsheet 28. For example, the topsheet may be composed of a meltblown or spunbonded web of polyolefin fibers. The topsheet may also be a bonded-carded-web composed of natural and/or synthetic fibers.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic and substantially nonwettable material, and the hydrophobic material may optionally be treated with a surfactant or otherwise processed to impart a desired level of wettability and hydrophilicity. In a particular embodiment of the invention, topsheet 28 can be a nonwoven, spunbond polypropylene fabric composed of about 2.8–3.2 denier fibers formed into a web having a basis weight of about 20 gsm (g/m$^2$) and density of about 0.13 gm/cc. The fabric can be surface treated with a selected amount of surfactant, such as about 0.28% TRITON X-102 surfactant available from Union Carbide, a business having offices in Danbury, Conn. The surfactant can be applied by any conventional means, such as spraying, printing, brush coating or the like.

The surfactant material, such as a conventional wetting agent, can be applied to a medical section of the topsheet layer 28 to provide a greater wettability of the medial section, as compared to a remainder of the topsheet layer 28. In particular configurations, the cross-directional width of the medial section can be substantially equal to or less than the cross-directional width of the surge management portion 46. In alternative configurations, the medial section width can be substantially equal to or less than a cross-directional spacing between a pair of adhesive strips or other bonds employed to secure the containment flap sections 144 onto topsheet 28 and to form a leak resistant barrier seal onto the backsheet 30.

The surfactant-treated medial section can be approximately centered with respect to the longitudinal centerline of the diaper, and can extend along substantially the entire length of the topsheet layer. Alternatively, the surfactant treated medial section can be constructed to extend along only a predetermined portion of the topsheet length.

In the various configurations of the invention, the fabric layer employed in the gusset-flap members 19 and/or the waist flaps 84, may, for example, be constructed of a fibrous material which is similar to the material comprising topsheet 28, or similar to the material comprising surge management portion 46. Examples of these materials include but are not limited to spunbond fabrics, meltblown fabrics, spunbond-meltblown laminates, spunbond-meltblown-spunbond (SMS) laminates, spunbond-meltblown (SM) laminates, spun-lace webs, thermal point bonded carded webs, through-air bonded carded webs, coform webs, and hydro-knit materials. Other conventional materials, such as polymer films, may also be incorporated into such barrier flap components. In particular aspects of the invention, the barrier flap components can be constructed of a material which is permeable only to gas, such as ambient air. Alternative configurations of the invention can include barrier flaps which are constructed of a material which is resistant to a passage of aqueous liquid, such as urine, therethrough. For example, the barrier flap sections of the gusset-flap members may include a fabric layer which is constructed of a spunbond-meltblown-spunbond (SMS) laminate material. For a particular example, the barrier flap sections of the gusset-flap members can be constructed of a SMS material having a basis weight of about 0.60–0.75 oz/yd$^2$ (about 20–25 g/m$^2$). The spunbond layers can composed of polypropylene fibers, and the meltblown layer can be composed of meltblown polypropylene fibers. Alternatively, the barrier flaps may be constructed using a spunbond fabric layer having a basis weight of about 0.4–1.0 oz/yd$^2$ (about 13–33 g/m$^2$). The spunbond fabric layer may consist of fibers made from polypropylene or a polypropylene/polyethylene copolymer composition.

Where a thermally bonded fabric is used as the fabric layer, it is desirable to minimize the amount of bonded area on the fabric to improve tactile and visual softness characteristics of the gusset-flap member. Preferably, the bonded area of the fabric is less than 25%. More preferably, the bonded area of the fabric is less than 15%. The percent bonded area can be measured by an analysis of an imprint of the bonding pattern produced by the bonding/embossing pattern die.

In the various configurations of the invention where selected materials or components, such as the barrier flaps provided by containment flap sections 144 and/or waist pocket sections 84, are configured to be permeable to gas while having a resistance and limited permeability to aqueous liquid, the liquid resistant material or component can have a construction which is capable of supporting a hydro-head of at least about 45 cm of water substantially without leakage therethrough. A suitable technique for determining the resistance of a material to liquid penetration is Federal Test Method Standard FTMS 191 Method 5514, 1978, or an equivalent thereof.

The backsheet 30 may be composed of a liquid permeable material, but preferably comprises a material which is configured to be substantially impermeable to liquids. For example, a typical backsheet can be manufactured from a thin plastic film, or other flexible liquid-impermeable material. Such "flexible" materials are compliant and will readily conform to the general shape and contours of the wearer's body. The backsheet 30 can help prevent the exudates contained in absorbent structure 32 from wetting articles such as bedsheets and overgarments which contact diaper 10.

In particular embodiments of the invention, backsheet 30 is a polyethylene film having a thickness of from about 0.012 millimeters (0.5 mil) to about 0.051 millimeters (2.0 mil). In the shown embodiment, for example, the backsheet is a film having a thickness of about 0.032 mm (about 1.25 mil). Alternative constructions of the backsheet may comprise a woven or non-woven fibrous web layer which has been totally or partially constructed or treated to impart a desired level of liquid impermeability to selected regions of the backsheet that are adjacent or proximate the absorbent body. For example, a clothlike backsheet may be composed of an approximately 0.5 oz/yd$^2$ (about 17 g/m$^2$) basis weight, polypropylene spunbond fabric which is laminated and thermally bonded to a stretch-thinned polypropylene film having a thickness of about 0.0006 inch (about 0.015 mm) and a film basis weight of about 14.5 g/m$^2$. Backsheet 30 typically provides the outer cover of the article. Optionally, however, the article may comprise a separate outer cover member which is in addition to the backsheet.

Backsheet 30 may optionally include a micro-porous, "breathable" material which permits vapors to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minn. The backsheet can also be embossed or otherwise provided with a matte finish to exhibit a more aesthetically pleasing appearance.

A parameter for determining the air-permeability or breathability of a material or component can be its water vapor transmission rate (WVTR). Where a material or component has a selected WVTR value, the WVTR for a sample can be calculated in general accordance with ASTM standard E96-80, or an equivalent thereof. In the determination of the WVTR, circular samples measuring three inches in diameter are cut from each of the test materials and a control, comprising of a piece of CELGARD® 2500 film, a microporous polypropylene film from Hoechst Celanese Corporation, a company having offices in Sommerville, N.J.

Three specimens are prepared for each material. The test dishes used in testing are number 681 VAPOMETER cups distributed by Thwing-Albert Instrument Company, a company having offices in Philadelphia, Pa. One hundred milliliters (ml) of distilled water are poured into each VAPOMETER cup and individual samples of the test materials and control material are place across the open tops of the individual cups. Screw-on flanges are then tightened to form a seal along the edges of each cup with no sealant grease used to apply the flange leaving the associated test material or control material exposed to the ambient atmosphere over a 6.5 centimeter (cm) diameter circle having an exposed area of approximately 33.17 square centimeters. The cups are then weighed and placed in a forced air oven set at a temperature of 37 degrees Celsius (100 degrees Fahrenheit). The oven is a constant temperature oven with external air circulating through it to prevent water vapor accumulation inside. A suitable forced air oven is, for example, a Blue-M POWER-O-MATIC 60 oven distributed by Blue M Electric Company, a company having offices in Blue Island, Ill. After 24 hours, the cups are removed from the oven and weighed again. The preliminary test water vapor transmission rate values are then calculated as follows:

$$\text{Test } WVTR \ (g/m^2 124 \text{ hrs}) = (\text{grams weight loss over } 24 \text{ hours}) \times 315.5$$

The relative humidity within the oven is not specifically controlled.

Under predetermined set conditions of 37 degrees Celsius (100 degrees Fahrenheit) ambient relative humidity to WVTR for the CELGARD® 2500 film has been determined to be 5000 grams per square meter for 24 hours ($g/m^2 124$ hrs). Accordingly, the control sample is run with each test and the preliminary test values are corrected to set condition using the following equation:

$$WVTR \ (g/m^2/24 \text{ hrs}) = (\text{Test } WVTR)/(\text{Control } WVTR) \times 5000 \ g/m^2/24 \text{ hrs.}$$

The size of the backsheet 30 is typically determined by the size of absorbent structure 32 and the exact diaper design selected. Backsheet 30, for example, may have a generally T-shape, a generally I-shape or a modified hourglass shape, and may extend beyond the terminal edges of absorbent structure 32 by a selected distance, such as a distance within the range of about 1.3 centimeters to 5.0 centimeters (about 0.5 to 2.0 inch), to provide side margins.

In particular aspects of the invention, the backsheet layer can have a maximum waistband width_A along the cross dimension 24, and a minimum crotch width_B at an intermediate portion of the backsheet layer, as representatively shown in FIG. 12. A quotient of the maximum waistband width_A divided by the minimum crotch width_B of the backsheet 30 is at least a predetermined value, such as a minimum value of at least about 1.6 Alternatively, the quotient can be at least about 1.8, and optionally, the quotient can be at least about 2 to provide further improved performance.

The backsheet layer can also have a length_K along which a cross-directional width of the backsheet is not more than a value_C, where the value_C is determined by the formula, $$(\text{value\_C}) = (0.8) \ast (\text{width\_B}) + (0.2) \ast (\text{width\_A}).$$

The length_K can be at least a minimum percentage of the overall length 180 of the article, such as about 30% of the article length. Alternatively, the length_K can be at least about 35% of the overall length of the article, and optionally can be at least about 40% of the overall length of the article to provide improved fit and conformance. In further aspects, the length_K can be not more than about 80% of the overall length of the article. Alternatively, the length_K can be not more than about 70%, and optionally can be not more than about 60% of the overall length of the article to provide improved performance.

The narrow crotch width of the backsheet layer 30 can advantageously reduce the amount of material in the crotch region of the wearer and help reduce excessive bunching of the article between the wearer's legs. As a result, there can be a closer, more leakage-resistant fit of the article against wearer's body in the crotch region.

The backsheet layer 30 can also include a front turn-out angle_θ which is within a selected range. The angle_θ may, for example, be defined from the tangent lines as shown in FIG. 12. The tangent lines can be drawn as extensions of the essentially straight line segments of the side contour 15 which lead into and out of the angled backsheet cutout nearest the front waistband portion of the article.

Alternatively, the angle_θ may be defined from a value_D and a value_E, which are shown in FIG. 12. The value_D is a equal to 80% of the maximum lateral cutout distance produced by the side edge contour 15 at the front waistband portion of the absorbent article. The maximum lateral cutout distance is a lateral distance measured at the location of the narrowest crotch width of the backsheet layer 30, and is the distance from the edge of the backsheet layer (at its narrowest crotch width location) to a line defined by the maximum outward width of the backsheet layer at the front waistband portion of the article. In the shown article having bilateral symmetry, the value_D corresponds to the distance between longitudinal line defining the outer limit of value_C, and the line defined by the maximum outward width of the backsheet layer at the front waistband portion of the article. The value_E measures the longitudinal distance from the start of the side edge contour 15 at the front of the absorbent article to the longitudinal location where 80% of the maximum lateral cutout distance is reached by the side edge contour 15 at the front of the article.

The value_H measures the longitudinal distance from the longitudinal point of minimum backsheet cutout (location where the backsheet layer has its narrowest crotch width) to the location along the longitudinal length where one-half of the distance of value_K has been covered. The value_G measures the lateral width of the backsheet at the location where the longitudinal distance of value_H terminates. The angle_θ may then be determined by taking the sum of 90 degrees plus the angle defined by the inverse tangent of the fraction (value_E/value_D), and then subtracting the angle defined by the inverse tangent of the quantity ((value_G −value_B)/(2×(value_H))).

In particular aspects of the invention, the angle_θ can be at least about 90 degrees, and optionally, can be at least about 115 degrees. In other aspects, the angle_θ can be not more than about 140 degrees, and optionally can be not more than about 135 degrees. The selected angle_θ can advantageously provide an improved fit on the wearer, particularly at the wearer's waist and leg regions, and can allow a more efficient manufacturing of the article on high-speed processing equipment.

The configurations of the backsheet 30 can provide desired coverage of the buttocks of the wearer while also providing a sufficiently independent operation of the gusset-flap members 19. As a result, the article can help provide an improved combination of fit by the backsheet and gasketing by the gusset-flaps. In particular, the leg gusset sections 142 can better conform to the wearer and improve leakage protection.

The topsheet 28 and backsheet 30 are connected or otherwise associated together in an operable manner. As used therein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in selected regions, such as in areas along the diaper periphery, by a suitable attachment mechanism (not shown), such as an adhesive, sonic bonds, thermal bonds or any other attachment mechanism known in the art. For example, a uniform continuous layer of adhesive, a patterned layer of adhesive, a sprayed pattern of adhesive or an array of separate lines, swirls or spots of construction adhesive may be used to affix topsheet 28 to backsheet 30.

It should be readily appreciated that the above-described attachment mechanisms may also be employed to interconnect and assemble together the various other component parts of the article described herein.

In the representatively shown embodiment of the invention (e.g. FIG. 1), the topsheet layer 28 is disposed and secured in facing relation with the backsheet layer 30 to retain and hold the retention portion 48 and the surge management 46 between the backsheet layer and the topsheet layer. The marginal side regions of topsheet layer 28 are operably connected to corresponding marginal side regions of the backsheet layer 30. Each of the attached marginal side regions of the topsheet and backsheet layers is located laterally outboard of its corresponding, associated side edge region of the surge management portion 46. In particular configurations of the invention, the topsheet 28 can include attached marginal end regions, which are located longitudinally outboard of the end edge regions of the retention portion 48 and/or surge management portion 46. Similarly, the backsheet 30 can include attached marginal end regions, which can be located longitudinally outboard of the end edge regions of the retention portion and/or surge management portion.

The leg elastic members, such as those provided by the elasticized leg gusset sections 142, are disposed adjacent the periphery of diaper 10 along each of the longitudinal side edge regions 20. The leg elastic members can be connected to either or both of the topsheet and backsheet layers to provide elasticized side margins of the diaper article, and can be arranged to draw and hold diaper 10 against the legs of the wearer to provide elasticized leg bands or leg cuffs. Waist elastic members, such as those provided by the flange section 82 of the waist member 80, may also be disposed adjacent either or both of the end edges of diaper 10 to provide elasticized waistbands.

The elastic members at the legband and waistband sections of the article are secured to the article in an elastically contractible condition so that in a normal under strain configuration, the elastic members effectively contract against the article. The elastic members can be secured in an elastically contractible condition in a number of ways; for example, the elastic members may be stretched and secured while the appointed component of the article is in an uncontracted condition. Alternatively, the component may be contracted, for example, by pleating, and the elastic members secured and connected to the component while the elastic members are in their relaxed or unstretched condition. Still other means, such as heat-shrink elastic material, may be used to gather the appointed component sections of the article.

The elastic members, such as elastomeric members 110, 118, 138 and 68, may have any of a variety of configurations. For example, the width of the individual elastic members may be varied from about 0.08 millimeters (0.003 inches) to about 25 millimeters (1.0 inches) or more. The elastic members may comprise a single strand of elastic material, or may comprise several parallel or non-parallel strands of elastic material, and the elastic members may be applied in a rectilinear or curvilinear arrangement. Where multiple strands are employed, the individual strands may be constructed to provide substantially equal elastic forces, or may be constructed to provide different elastic forces. For example, the individual strands may be of different diameter or other size, or may be configured with different amounts of elongation to thereby provide a gradient or other variation of elastic tensions. Where the strands are non-parallel, two or more of the strands may intersect or otherwise interconnect within the elastic member. The elastic members may be affixed to the appointed diaper components in any of several ways which are known in the art. For example, the elastic members may be ultrasonically bonded, heat and pressure sealed using a variety of bonding patterns, or adhesively bonded to diaper 10 with selected patterns of hotmelt or other type of adhesive. For example, sprayed or swirled adhesive patterns may be employed.

In particular embodiments of the invention, for example, each elastic strand is typically within the range of about 77–1500 decitex (dtx). In addition, elastics may be generally straight or optionally curved. For example, the curved elastics can be inwardly bowed toward the longitudinal centerline of the diaper. In particular arrangements, the curvature of the elastics may or may not be configured or positioned symmetrically relative to the lateral centerline of the diaper. The curved elastics may have an inwardly bowed and outwardly bowed, reflex-type of curvature, and the length-wise center of the elastics may be offset by a selected distance toward either the front or rear waistband of the diaper to provide desired fit and appearance.

Conventional articles have incorporated various barrier flap structures, such as the containment flaps 144 and the waist pocket sections 84, at their waistband and/or legband regions. For example, such articles have typically incorporated a single or multi-layer piece of material, such as polymer films and film-nonwoven laminates, at the waistband portion of the article along the lateral cross-direction to form a waist flap or dam. The materials, however, typically exhibit similar behavior. When the materials are stretched, they have a tendency to neck down, thereby reducing their effective widths. As they neck down, they tend to form relatively large corrugations or furrows which extend substantially along the direction of stretching. The presence of such corrugations can cause the barrier flaps, particularly the waist flaps, to collapse upon themselves, thereby reducing the ability to remain open to receive and trap bodily waste materials. Additionally, when the conventional materials contract, they tend to decrease in overall stiffness, and this decrease in composite stiffness can again allow the barrier flaps to fold over or collapse upon themselves, thereby reducing their effectiveness.

It has been discovered that particular barrier flap structures, such as laminates incorporating individual and separated elastic strands, can provide structures which can overcome the shortcomings of prior structures. When stretched, the stranded laminates of the invention substantially avoid the undesired stretch-wise corrugating effect typically seen across the plane of the barrier flap and along the intended direction of stretch. Desirably, the amount of stretching does not exceed the amount of elongation at which the elastic strands were assembled into the laminate. When fully stretched and elongated, the stranded laminate can lay substantially flat. As the stranded laminate relaxes and elastically contracts, fine corrugations of sufficient size and frequency can be provided with the furrows or valleys of the corrugate generally aligned to extend substantially perpendicular to the direction of the contraction. The fine corrugations can enhance the stiffness of the flap structure and can improve its ability to remain open to receive waste materials. The stranded laminates of the present invention substantially avoid necking when stretched. Additionally, the geometry of the stranded laminates themselves play an important role in the performance of the materials when employed as a barrier dam structure, such as the shown waist dam and/or containment flap structures. The placement of the strands can also play a role in the functionality of the various configurations of the laminas.

It has been found, however, that the identifications of conventional types of materials or families of materials have not been adequate for deriving barrier flap structures that are sufficiently effective and reliable. It has been discovered that the performance and effectiveness of the barrier flap structure is dependent upon particular combinations of properties and behavior characteristics of the materials employed to assemble and construct the composite barrier flaps. For example, the incorporation of a flap composed of a polyurethane film or film laminate at the article waistband, and the placement of a flap composed of a SMS (spunbond-meltblown-spunbond) nonwoven fabric laminate at the article waistband have not reliably provided a sufficiently effective barrier flap structure. It is important to further configure the materials with particular physical properties, and one of the desired physical properties is the stiffness of the flap member.

The desired stiffness of the barrier flap member can be achieved in a variety of ways. For example, contributing factors include the basis weight of the flap materials, the stiffness or modulus of the individual components, the presence of adhesive or other bonding materials added to laminates within the flap member, the pattern and distribution of the applied adhesive or bonds, the presence of welding or ultrasonic treatments, the number and the elongation of the individual elastic strands employed in the barrier flap structure, the geometry of the strand placement within barrier flap, the presence and alignment of corrugations within the barrier flap, and the number of layers of components incorporated within the barrier flap.

Particular aspects of the invention can include distinctive combinations of component sizes and component stiffnesses. For example, the containment flap stiffness can have a Gurley stiffness value, as measured in a sample taken along the lateral cross-direction 24 of the article, which is at least about 10 milligrams-force (mgf). In other aspects, the cross-directional Gurley stiffness in the containment flap section can be not more than about 250 mgf, and optionally, can be not more than about 60 mgf to provide improved benefits. In addition, the leg gusset section can have a Gurley stiffness value, as measured in a sample taken along the lateral cross-direction 24 of the article, which is at least about 11 milligrams-force (mgf), and desirably is at least about 30 mgf. In further aspects, the cross-directional Gurley stiffness in the leg gusset section can be not more than about 250 mgf, and optionally, can be not more than about 120 mgf to provide improved benefits. In the various configurations of the invention, the Gurley stiffness of the leg gusset section (as measured with respect to a sample taken along the lateral cross-direction of the absorbent article) is substantially equal to or greater than the cross-directional Gurley stiffness of the containment flap section of the gusset-flap component.

With reference again to FIGS. 1, 2 and 3, the shown diaper article 10 may optionally have an elasticized waistband provided by a waist pocket member 80 which can include a laterally and longitudinally extending flange section 82, and a laterally and longitudinally extending barrier flap or pocket section 84. The flange section can, for example, be connected to the bodyside surface of the topsheet 28. The flap or pocket section 84 of the waist pocket member 80 includes a substantially fixed edge portion 102 which is secured to the article along and immediately adjacent the boundary of the flange section 82, and includes an elasticized, gathered moveable edge portion 104, which is longitudinally spaced from the fixed edge portion 102 by a selected distance. The pocket section thereby provides an operable waist dam and waist flap construction. The pocket section also includes a substantially liquid impermeable pocket barrier layer 106, and a pocket fabric layer 108 which is connected in facing relation with the pocket barrier layer. The pocket fabric may, for example be composed of a woven or nonwoven fabric, and in the shown arrangement, the fabric layer is desirably a nonwoven. A plurality of separate, laterally extending pocket elastic members 110 are sandwiched and operably connected between the pocket barrier layer 106 and the pocket fabric layer 108 to provide an elasticized waist pocket composite 112, which is gathered substantially along the lateral cross-direction 24 and is elastically stretchable at least along the cross-direction. Similarly, elastic members 118 can be arranged within the composite 112 to operatively elasticize the flange section 82. The shown arrangement includes elastics members which are aligned substantially parallel to one another, but optionally can include other separated configurations and alignments of the elastics. Desirably, the fabric layer 108 is arranged for placement against the wearer's skin, although the barrier layer 106 may optionally be appointed for placement immediately adjacent the wearer's skin. Suitable configurations for the waist pocket member 80 are described in U.S. patent application Ser. No. 560,524 which was filed Dec. 18, 1995 by D. R. Laux et al. and entitled AN ABSORBENT ARTICLE WITH IMPROVED WAIST ELASTIC AND CONTAINMENT SYSTEM, the entire disclosure of which is incorporated herein by reference in a manner that is consistent herewith.

With reference to FIGS. 4, 5, 6, and 7, the gusset-flap barrier layer 174 can be composed of a variety of materials, such as polymer films, fabrics or combinations thereof, having a relatively low permeability to aqueous liquid. Desirably, the barrier layer is substantially liquid impermeable. The barrier layer may also be air-permeable or breathable. Thus, the polymer films may be breathable or non-breathable, and may, for example, be composed of polyolefins, polyesters, polyamides and the like, as well as combinations thereof. The fabrics may be breathable or non-breathable be woven or nonwoven, and the nonwoven materials can include spunbond fabrics, meltblown fabrics, spunbond-meltblown (SM) fabrics, spunbond-meltblown-spunbond (SMS) fabrics, calendered nonwoven sheets and the like, as well as combinations thereof. With respect to the passage of liquid through its thickness, the barrier layer is constructed to exhibit a hydrohead of resistance which is sufficient to provide an operably effective barrier against the passage of liquids, such as urine.

In particular aspects, the barrier layer can have a selected water vapor transmission rate (WVTR), such as a WVTR of at least a minimum of 300 grams per square meter per 24 hours ($g/m^2/24$ hr). The barrier layer 174 can alternatively have a WVTR of at least about 800 $g/m^2/24$ hrs, and can optionally have have a WVTR of at least about 3000 $g/m^2/24$ hrs to provide improved benefits.

The gusset-flap barrier layer 174 may, for example, be composed of a cast, embossed film having a thickness of about 0.015 mm (about 0.0006 inch), such as a CT XEM400.1 film; or a blown film having a thickness of about 0.010 mm (about 0.0004 inch), such as an XSF-367 film. Suitable films are available from Huntsman Packaging, (formerly Consolidated Thermoplastics), a business having offices in Chippewa Falls, Wis. The barrier layer may also be composed of a stretch-thinned film having a thickness of about 0.0089 mm (about 0.00035 inch), such as an XP1024A film available from Huntsman Packaging (formerly Edison Plastics), a business having other offices in Macalester, Okla. Alternatively, the barrier layer may be constructed with a breathable film having a thickness of about 0.0050 mm (about 0.0002 inch), such as a BF-303 film available from Exxon Plastics, a company having offices in Houston, Tex.

The gusset-flap fabric layer 176 is desirably a substantially continuously extending layer, and the gusset region 136 of the fabric layer is desirably contiguous with the containment flap region 63. In addition, the fabric layer 176 can be a substantially unsegmented, unitary layer. The gusset-flap fabric can be composed of a variety of materials, such as a fine denier, low basis weight, nonwoven fabric material. Examples of suitable nonwoven fabrics include polypropylene spunbond materials, bicomponent polypropylene-polyethylene spunbond materials, meltblown materials, SMS materials, through-air-bonded carded webs, point-bonded bonded-carded webs and the like, as well as combinations thereof. In particular arrangements, the fabric may be composed of a spunbond polypropylene which includes about 0–8% polyethylene copolymer, and desirably includes about 3% polyethylene copolymer.

In desired arrangements, the gusset-flap fabric layer 176 can have a basis weight of not less than about 3.4 $g/m^2$ (about 0.1 $oz/yd^2$). Alternatively, the basis weight can be not less than about 10.2 $g/m^2$ (about 0.3 $oz/yd^2$), and optionally can be not less than about 13.6 $g/m^2$ (about 0.4 $oz/yd^2$). In other aspects, the fabric layer 136 can have a basis weight of not more than about 272 $g/m^2$ (about 8 $oz/yd^2$). Alternatively, the basis weight can be not more than about 136 $g/m^2$ (about 4 $oz/yd^2$), and optionally can be not more than about 34 $g/m^2$ (about 1 $oz/yd^2$).

For example, the gusset-flap fabric layer can be a nonwoven fabric composed of polypropylene fibers wherein the fiber denier is not more than about 5 denier, and the fabric basis weight is about 17 $g/m^2$ (about 0.5 $oz/yd^2$). Alternatively, the fiber denier in the fabric layer can be not more than about 3 denier, and optionally can be not more than about 2.5 denier.

Desired arrangements of the article of the invention can be configured with each gusset-flap 19 connected directly or indirectly to an appointed section of an inwardly facing, bodyside surface of the topsheet layer 28. Optionally, the gusset-flap can be connected directly or indirectly to an appointed surface region of the backsheet layer 30. In the embodiment illustrated in FIG. 1, the elasticized gusset-flaps 19 extend along substantially the complete length of the intermediate region 16 of diaper 10. Alternatively, the gusset-flap members may extend the entire length of diaper 10, or any other length suitable for providing the arrangement of elastically contractible lines desired for the particular diaper design.

In particular, each gusset-flap is connected along its associated, outwardly concave, terminal side edge contour 15 of the backsheet layer. Each of the side edge contours can have a longitudinal length 54 which desirably extends completely through the crotch region 18, and which may extend along at least about 20 percent of a total longitudinal length 180 of the article. In further configurations, the longitudinal length 54 of the side contour can be at least about 30 percent, alternatively can be at least about 40 percent, and optionally can be up to 100 percent of the total longitudinal length 180 of the article.

The leg elastics of the shown diaper 10 can be provided by the distinctive leg gusset sections 142 of the gusset-flaps 19. Each leg gusset section 142 can have a length thereof which extends along at least about 20 percent of the total longitudinal length 180 of the article. In other configurations, each leg gusset section 142 can extend along at least about 30 percent, and alternatively at least about 40 percent of the longitudinal length 180 of the article to provide improved effectiveness. If desired, each leg gusset section can extend along a length which can be up to 100 percent of the total longitudinal length of the article to provide further gasketing and containment. Alternatively, each leg gusset section can extend along a length which is not more than about 80 percent, and optionally is not more than about 70 percent of the total longitudinal length of the article to provide desired performance.

Additionally, each leg gusset section 142 can be in a bridging configuration across its associated, concave side edge contour 15 of the backsheet layer along a length 182 which is at least about 20 percent of the longitudinal length 180 of the article. In other configurations, each leg gusset section 142 can be in a bridging configuration across its associated, concave side edge contour 15 of the backsheet layer along a length 182 which is at least about 30 percent, and alternatively is at least about 40 percent of the extent of the longitudinal length 180 of the article to provide improved effectiveness. If desired, each leg gusset section can be in a bridging configuration along a length which can be up to 100 percent of the total longitudinal length of the article to provide further gasketing and containment. Alternatively, each leg gusset section can be in a bridging configuration along a length which is not more than about 80 percent, and optionally is not more than about 70 percent of the total longitudinal length of the article to provide desired performance and cost effectiveness.

It has also been found that the length of the effective elastic leg gathering of the leg gusset section 144 of the gusset-flap 19 can be important to the performance of the absorbent article. Accordingly, the leg gusset section can have an effective, free elastic length 156 which is the average, continuous longitudinal length of the first arrangement of leg elastic members 138 which are not cut or otherwise deadened by the outboard deadening array 158, or by any attachments which would substantially deactivate the first elastic members 138. The effective free elastic length 156 of the leg gusset section is determined while the diaper is laid out in its fully extended form. In particular aspects the effective free elastic length 156 can be at least about 44% of the overall, total length 180 of the article. The effective free elastic length 156 can alternatively be at least about 52% of the overall article length 180, and optionally, can be at least about 60% of the overall article length provide improved performance. The effective free elastic length 156 may be substantially equivalent to the overall article length 180, but such a configuration can cause excessive curling of the article waistband portions. In desired aspects, the effective free elastic length 156 can be not more than about 90% of the overall length of the article. Alternatively, the effective free elastic length can be not more than about 80% of the overall length of the article to provide further improved benefits.

In particular aspects of the invention, the gusset-flaps 19 may be configured to substantially avoid intersecting the locations of the waist pocket members 80. Accordingly, the gusset-flaps can be constructed to terminate at positions which are spaced away from the terminal edges of the pocket sections 84 of the waist pocket members.

Figure 6:
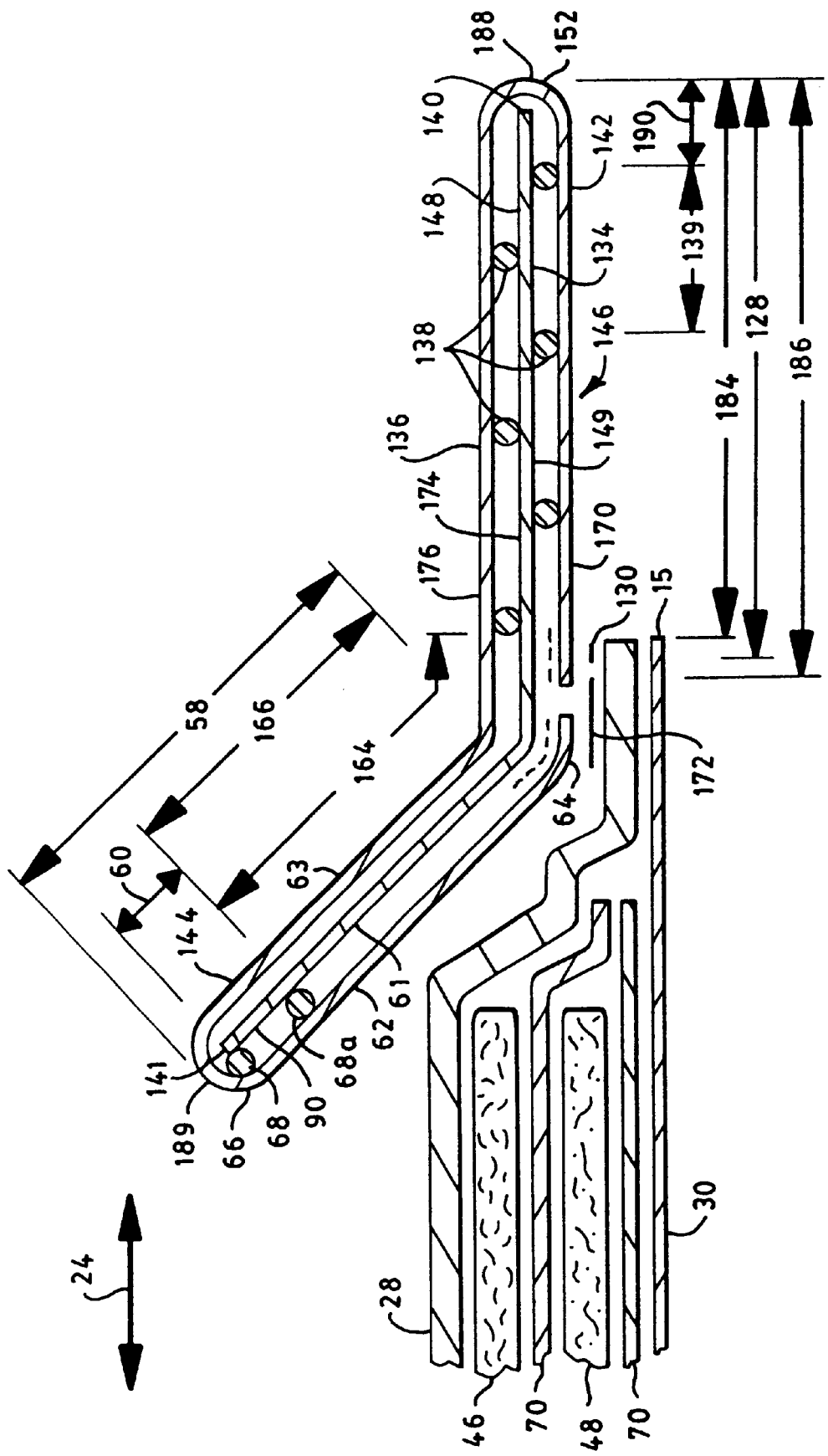
FIG. 6 representatively shows a schematic, expanded, lateral cross-sectional view of a configuration of the gusset-flap member where the gusset flap barrier layer extends into the containment flap section.

With reference to FIGS. 1, 4 and 6, each of the side margins of the backsheet layer 30 generally defines a plane thereof, and each of the leg gusset sections 19 is constructed to extend past and beyond its associated concave side edge contour 15 of the backsheet layer 30 by a selected skirting distance 184, and in an arrangement which lies substantially within and substantially parallel to the plane of its associated backsheet side margin.

In the various arrangements of the invention, each leg gusset section 142 can include a leg gusset region 134 of the barrier layer 174, a leg gusset region 136 of the fabric layer 176 and a first arrangement of a first plurality of separate, longitudinally extending elastomeric members 138 sandwiched between the leg gusset region of the barrier layer and the cooperating, corresponding portions of the leg gusset regions of the fabric layer to provide an elastomeric composite which is substantially longitudinally gathered. In particular arrangements, the barrier layer region 134 and the fabric layer region 136 can be substantially coextensive. The elastomeric members can be arranged in any desired alignment or configuration, such as parallel, non-parallel, straight, curvilinear or combinations thereof. Alternatively, the complete leg gusset portion of the gusset-flap, or the containment flap portion of the gusset-flap, or the entire gusset-flap may also be placed in the absorbent article in a parallel, non-parallel, straight, curvilinear, or any combination thereof. Desirably, the fabric layer region 136, particularly the folded over, outboard side portion 170, is arranged for placement against the wearer's skin. Optionally, the barrier layer region 134 may be appointed for placement immediately adjacent the wearer's skin.

In particular aspects, the illustrated barrier layer region 134 is substantially coextensive with its corresponding leg gusset section 142 at least in the portion of the leg gusset section which bridges and spans across the C-shaped gap formed by terminal edge of the corresponding side contour of the backsheet 30. The barrier layer 174 may or may not extend into the adjacent containment flap section 144 of the gusset-flap member, as desired.

With reference to the representative arrangements shown in FIGS. 4 and 6, the leg gusset region 136 of the fabric layer 176 can be positioned and joined immediately adjacent to the first, relatively inward surface 148 of the barrier layer 174. The outboard side portion 170 of the fabric layer extends beyond the first, relatively outboard side edge 140 of the barrier layer 174, and the fabric layer has an appointed, first folding line or region 188 which is positioned generally adjacent to the side edge 140 of the barrier layer. The fabric layer side portion 170 is operatively folded and wrapped around the barrier layer side edge 140 to thereby enclose the resultant wrapped edge of the barrier layer. The fabric layer side portion 170 then extends along the second major surface 149 of the barrier layer 174 in a direction toward the center of the article. Desirably, the fabric side portion 170 overlies a substantial entirety of the second major surface 149 of the barrier layer region 134 in the leg gusset section 142, and substantially completely covers the second major surface of the portion of the barrier layer which is located in the leg gusset section 142. Accordingly, the fabric side portion 170 can be interposed between the barrier layer and the wearer's skin.

The folding line 188 is spaced from the first edge 140 of the barrier layer by a distance 190 (FIG. 6) of not more than about 8 mm. Alternatively, the folding line 188 is spaced from the first edge 140 of the barrier layer by a distance which is not more than about 4 mm and optionally is not more than about 2 mm to provide improved performance. Desirably, the spacing distance 190 is substantially zero. If the spacing distance 190 is too large, there may be excessive wicking or leakage of liquids around the edge of the barrier layer.

Figure 9:
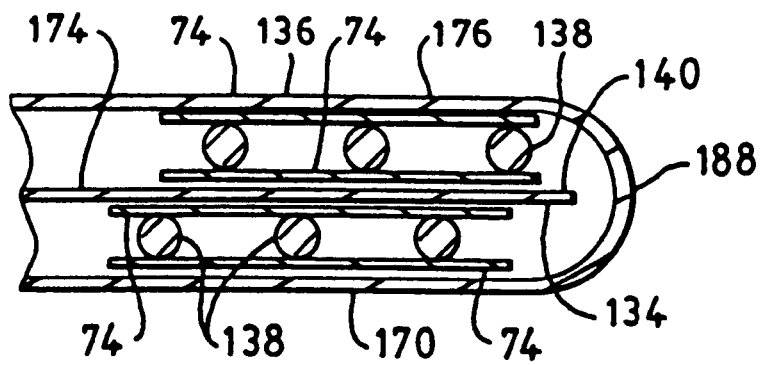
FIG. 9 representatively shows a schematic of a portion of an expanded, lateral cross-sectional view showing distributions of adhesive which bond the elastomeric members into the leg gusset portion the gusset-flap member.

Each of the elastic members 138 of the leg gusset section 142 are sandwiched between the barrier layer 174 and at least a portion of the fabric layer 176 in the leg gusset section of the gusset-flap 19. Each elastic member is attached to at least one of the barrier and fabric layers with a selected pattern of bonding, such as a pattern of adhesive. In particular arrangements, the elastic members 138 can be attached with one or more individual strips of adhesive 74, as representatively shown in FIGS. 9 and 10. Each adhesive strip 74 is configured to attach one or more of the elastomeric members 138 to at least one of the barrier and fabric layers. The strips of adhesive may also be configured such that the adhesive strip 74 covers either a portion or all of the circumference of the elastomeric members 138.

Figure 10:
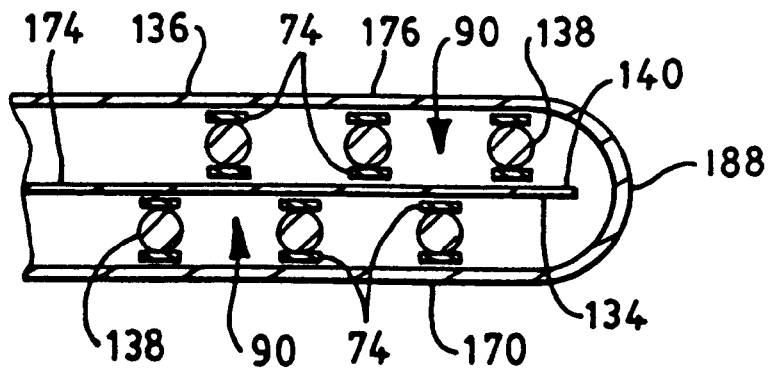
FIG. 10 representatively shows a schematic of a portion of an expanded, lateral cross-sectional view of a distribution of individual adhesive strips which attach the elastomeric members into the leg gusset portion the gusset-flap member.

In a particular aspect of the invention, each individual adhesive strip can be spatially separated from laterally adjacent adhesive strips by a discrete distance, as representatively shown in FIG. 10. With the illustrated arrangement, each adhesive strip 74 is configured to attach substantially a one of the elastomeric members 138 to at least one of the barrier and fabric layers, and the barrier layer 174 and the fabric layer 176 in the leg gusset section 142 are substantially unattached to each other at intermediate regions 90 located between immediately adjacent members of the first plurality of elastomeric members 138. Thus, each elastic member of the first plurality of elastomeric members 138 in each of the leg gusset sections 142 can be attached to at least one of the barrier layer 174 and/or fabric layer 176 with a substantially separately provided strip of adhesive 74. The individual, spatially separated adhesive strips substantially avoid touching one another. As a result, the substantially unattached intermediate regions 90 can blouse and more effectively form a cushioning topography.

Figure 11:
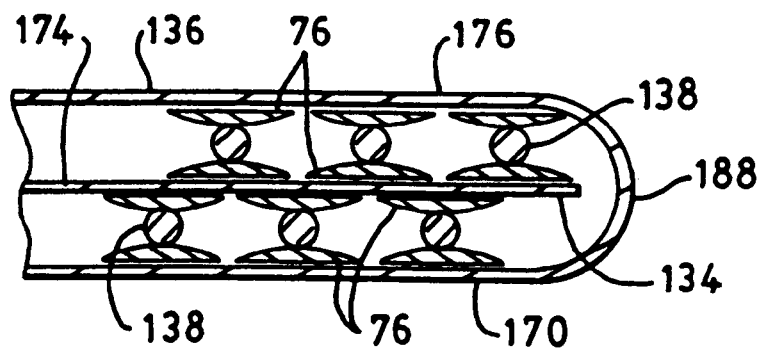
FIG. 11 representatively shows a schematic of a portion of an expanded, lateral cross-sectional view of another pattern distribution of adhesive add-ons which attach the elastomeric members in the leg gusset portion of the gusset-flap member.

In other arrangements of the invention representatively shown in FIG. 11, an adhesive pattern distribution 76 can be configured to concentrate the placement of adhesive at the locations of the elastic members 138, while delivering significantly reduced amounts of adhesive is in the areas between the elastic members 138, in the boundary space 164 between the containment flap elastics and the leg gusset elastics, and/or in the folding line area 188. The strips of adhesive may also be configured such that the adhesive strip 74 covers either a portion or all of the circumference of the elastomeric members 138. In additional aspects, the barrier layer 174 and the fabric layer 176 in the leg gusset section 142 can be attached to each other with a lesser, reduced adhesive amount at one or more of the intermediate areas which are interposed between immediately adjacent members of the first plurality of elastomeric members 138, as compared to the adhesive amount located at the positions of the first plurality of elastomeric members to secure and laminate the first plurality of elastomeric members. Similarly, where the barrier layer extends into the containment flap section 144, the barrier layer 174 and the fabric layer 176 in the containment flap section 144 can be attached to each other with a reduced adhesive amount at one or more of the intermediate areas which are interposed between immediately adjacent members of the second plurality of elastomeric members 68, as compared to the adhesive amount located at the positions of the second plurality of elastomeric members to secure and laminate the second plurality of elastomeric members.

Adhesive strips 74 or adhesive patterns 76 may also be used to attach elastomeric members 68 where the elastomeric members attach only to the fabric layer 174. The adhesive strips or adhesive patterns may wrap around all or at least a part of the circumference of the elastomeric members 68 when the elastomeric members 68 attach only to the fabric layer 176. This method of attachment for the elastomeric members 68 can allow for a cushioning topography in the containment flap section 144 of the gusset-flap 19 when the containment flap section does not contain the barrier layer 134.

With regard to the containment flap section 144, the second arrangement of at least one elastomeric member can be attached to at least one of the gusset-flap barrier and fabric layers 174, 176 with an increased amount of adhesive, as compared to the amount of adhesive located in the boundary space 164 between the first arrangement of leg-gusset elastics 138 and the second arrangement of containment flap elastics 68. Where the containment flap section 144 includes a second arrangement having a second plurality of elastomeric members, the elastomeric members can be attached to at least one of the gusset-flap barrier and fabric layers 174, 176 (particularly the fabric layer) with an increased, greater amount of adhesive, as compared to the amount of adhesive located at intermediate regions which positioned between immediately adjacent members of the second plurality of containment flap elastics. Where the barrier layer 174 extends into the containment flap section 144 and the second arrangement of containment flap elastics includes a second plurality of elastomeric members 68, the second plurality of elastomeric members can be laminated to the gusset-flap barrier and fabric layers with a greater amount of adhesive, as compared to the adhesive amount located at intermediate regions which positioned between immediately adjacent members of the second plurality of containment flap elastics.

While such arrangements may or may not have a discrete spacing between the area array of applied adhesive 76, it has been noted that this arrangement can provide sufficient adhesive bonding without unduly stiffening the leg gusset portion of the gusset-flap composite. This arrangement can also form a more cushioning topography in the leg gusset portion of gusset-flap.

Suitable techniques for applying a desired pattern of adhesive are described in U.S. Pat. No. 5,340,648 entitled ELONGATED ELEMENT COMPRISING HELICALLY PATTERNED ADHESIVE granted Aug. 23, 1994 to N. Rollins et al; U.S. Pat. No. 5,501,756 granted Mar. 26, 1996 to N. Rollins et al.; and U.S. Pat. No. 5,507,909 granted Apr. 16, 1996 to N. Rollins et al. The entire disclosures of these documents are incorporated herein by reference in a manner that is consistent herewith.

Figure 7:
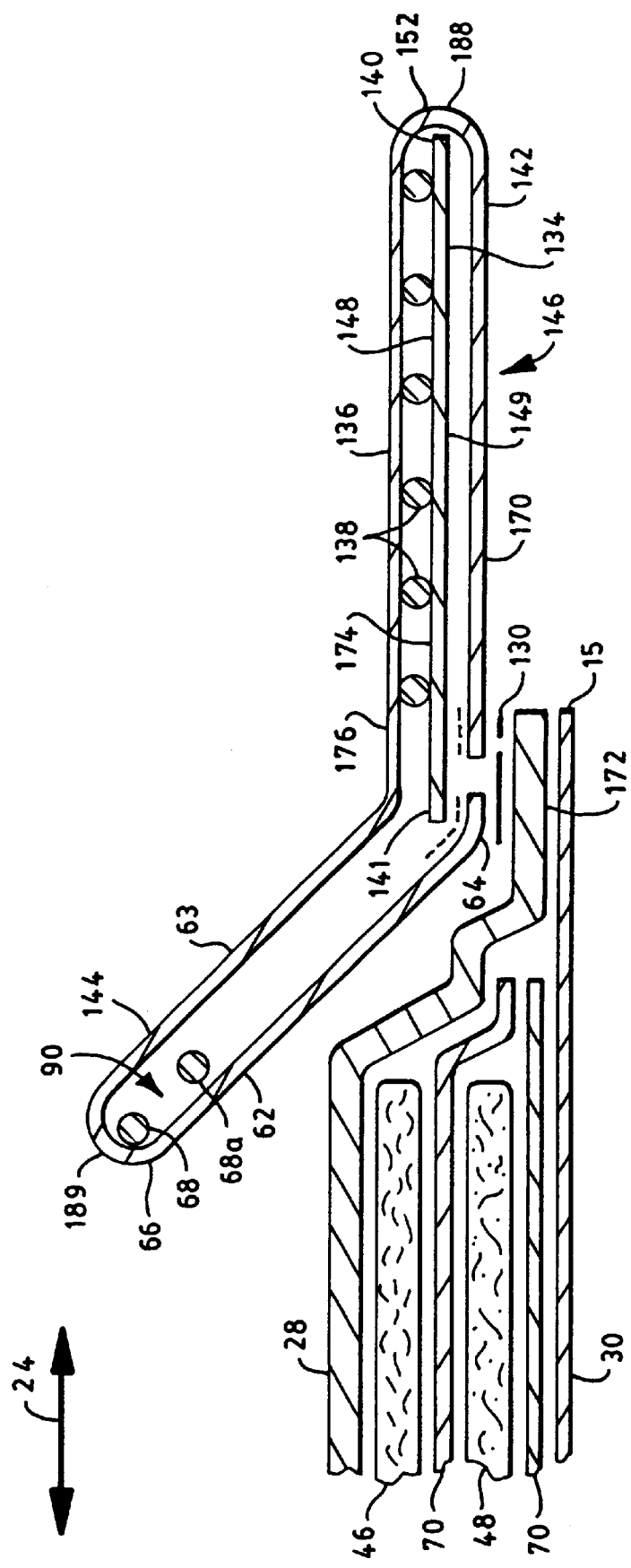
FIG. 7 representatively shows a schematic, expanded, lateral cross-sectional view of an alternative configuration of one of the gusset-flap members taken through the crotch section of the article.
Figure 8:
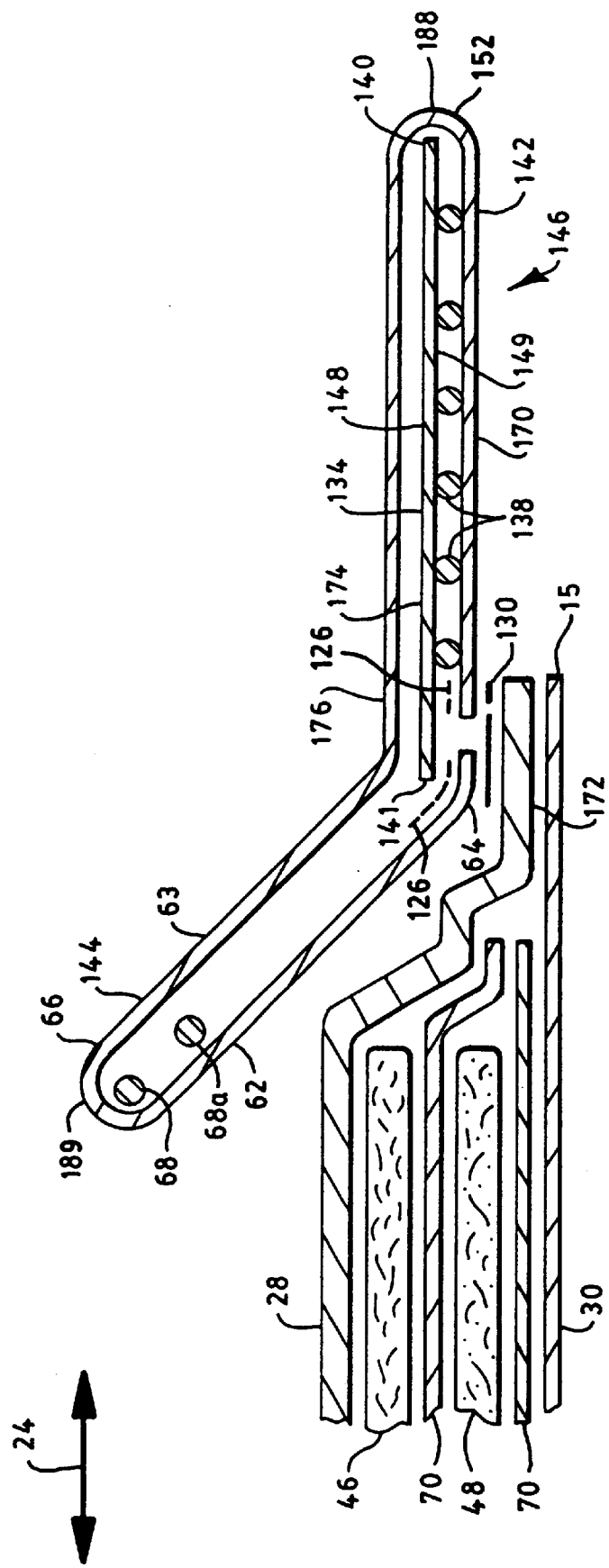
FIG. 8 representatively shows a schematic, expanded, lateral cross-sectional view of still another arrangement of the gusset-flap member.

All of the elastomeric members 138 can be attached on one single surface of the leg gusset region 134 of the barrier layer 174. For example, all of the elastomeric members 138 can be attached on the first major surface 148 and covered by the primary, base portion of the leg gusset region 134 of the fabric layer 176 (FIG. 7). Alternatively, all of the elastomeric members 138 can be attached on the second major surface 149 and covered by the outboard side portion 170 of the fabric layer (FIG. 8).

In another aspect, each of the leg gusset sections 142 can be configured with the first arrangement of elastomeric members 138 including a first sub-set of laterally spaced-apart elastomeric members joined to the first major surface 148 of the barrier layer 174, and a second sub-set of laterally spaced-apart elastomeric members joined to the second major surface 149 of the barrier layer (FIGS. 4 and 6). In desired arrangements, the first sub-set of elastomeric members can be laterally offset and staggered with respect to the second sub-set of elastomeric members. More particularly, the first sub-set of elastomeric members can be arranged with a first set of gaps between adjacent members, and the second sub-set of elastomeric members can be arranged with a second set of gaps between adjacent members. When observing across the thickness dimension of the barrier layer 174, the first sub-set of elastomeric members are substantially aligned with the second set of gaps, and the second sub-set of elastomeric members are substantially aligned with the first set of gaps.

In yet another aspect of the invention, adjacent elastomeric members 138 can have a spacing distance 139 (FIG. 6) therebetween which is not less than about 1 mm. Alternatively, the spacing distance can be not less than about 3 mm, and optionally can be not less than about 4 mm. In further aspects of the invention, the adjacent elastomeric members 138 can have a spacing distance 139 therebetween which is not more than about 45 mm. Alternatively, the spacing distance can be not more than about 35 mm, and optionally can be not more than about 25 mm.

The elastomeric members 138 within each leg gusset section 142 can be configured to provide for a composite elastic tension which is not less than about 50 grams-force when the leg gusset section composite is stretched to a length which is 90 percent of its substantially flat-out, uncontracted, extended length. The composite elastic tension can alternatively be not less than about 75 grams-force and optionally can be not less than about 100 grams-force to provide an improved combination of comfort and containment. In other aspects of the invention, the elastomeric members 138 within each leg gusset section 142 can be configured to provide for a composite elastic tension which is not more than about 300 grams-force when the leg gusset section composite is stretched to 90 percent of its flat-out, uncontracted length. The composite elastic tension can alternatively be not more than about 250 grams-force and optionally can be not more than about 200 grams-force to provide desired combinations of comfort and containment.

In desired configurations, each leg gusset section 142 can extend laterally beyond its associated side edge contour 15 of the backsheet layer 30 by a skirting distance 184 of not less than about 3 mm. Alternatively, the skirting distance can be not less than about 6 mm and optionally can be not less than about 9 mm, at least within the crotch section 18 of the article. In other aspects of the invention, each leg gusset section 142 can extend laterally beyond its associated side edge contour 15 of the backsheet layer 30 by a skirting distance of not more than about 100 mm. Alternatively, the skirting distance 184 can be not more than about 50 mm, and optionally can be not more than about 35 mm, at least within the crotch section 18 of the article, to provide improved comfort and gasketing. It is also desirable to configure the skirting distance to provide a substantially complete coverage of the buttocks of the wearer.

The various configurations of the leg gusset section 142 can provide a plurality of separate, longitudinally extending elastomeric members which are laterally spaced outboard from the longitudinally extending, terminal side edge of the backsheet layer by a discrete distance, at least within the crotch region of the article. Such laterally spaced elastomeric members can substantially avoid having a direct connection to said backsheet layer and can substantially avoid providing a direct gathering of said backsheet layer in its crotch region.

As representatively shown in FIGS. 4 and 6, each leg gusset section 142 is connected to the article, particularly with the bodyside surface of topsheet 28, with a leg gusset attachment, such as provided by gusset-flap attachment 172. The leg gusset attachment holds the gusset section 142 substantially parallel to a plane generally defined by its associated side margin of the backsheet 30. More particularly, the gusset attachment includes an article attachment which secures the leg gusset section 142 to the article adjacent to its associated outwardly concave terminal side edge contour 15 of the backsheet layer 30 along substantially an entire length of the side edge contour within which the leg gusset 142 and its correspondingly associated side edge contour 15 are coextensive. In particular aspects of the invention, the securement of each gusset section to the article substantially ends at a location which is laterally outboard of the absorbent body structure 32, at least within the crotch portion 18 of the article. Accordingly, the securement of the leg gusset section to the crotch portion article substantially ends at a location which is laterally outboard of the retention portion 48. Additionally, the securement of the gusset section 142 to the crotch portion of the article can substantially end at a location which is laterally outboard of the wrapsheet 70. In the shown arrangements, for example, the leg gusset attachment can have a generally U-shape configuration, with the bottom of the U-shape extending generally longitudinally and the two arms of the U-shape extending generally laterally. The shown U-shape is angular, but may be non-angular, if desired.

With reference to FIGS. 1 and 4, further aspects of the invention can include an additional gusset perimeter bond 130 which attaches a terminal side edge of the topsheet 28 and/or backsheet 30 to the leg gusset section 142 at least within the crotch region of the article. The perimeter bond attachment 130 is positioned adjacent to and laterally outboard from each gusset-flap attachment. Each perimeter bond attachment 130 is configured to secure its associated leg gusset section 142 to the article beside its corresponding, outwardly concave terminal side edge contour 15 of the article along at least a partial length of the terminal side edge contour of the backsheet layer 30. The perimeter bond attachment 130 extends generally inboard from a terminal side edge 50 of the backsheet layer 30 adjacent an article juncture region 52. As representatively shown, the generally inboard direction of the perimeter bond attachment may include at least a longitudinal vector component, and can include lateral and longitudinal vector components. The article juncture regions 52 are where an overlapping portion of an outboard, terminal side edge 152 of each leg gusset section 144 intersects across its corresponding terminal side edge contour 50 of the backsheet layer, and where the overlapping portion of the outboard edge 152 of the leg gusset section is superposed over an inward, bodyside surface of the backsheet layer 30.

Desired configurations of the invention can include a perimeter bond attachment 130 which is at least partially located in the intermediate portion 16 of the article, and is placed in the proximity of the side edge contour 15. In particular arrangements, the perimeter bond attachment 130 can have an essentially straight shape (e.g. FIG. 1). In other configurations, the perimeter bond attachment can substantially follow the shape of the deepest concave sections of the side edge contour 15, and each longitudinal end of the perimeter bond attachment can then have an essentially straight-line shape along the length-wise direction 26, as representatively shown in FIG. 16. In addition to the perimeter bond attachment 130, the article of the invention can include a leg gusset outboard securement 160 and/or a containment flap distal securement 79. In a particular configuration, the outboard securement 160 and/or distal securement may be discrete attachments and may be separated away from the perimeter bond 130. Another aspect of the invention may have either the outboard securement 160 or the distal securement 79 joined to their correspondingly proximate, perimeter bond 130. In desired arrangements of the invention, the leg gusset outboard securement 160 and containment flap distal securement 79 can attach the gusset-flap 19 to the article with arrangements in which the securements do not degrade the performance in the waistband portions of the article.

Each leg gusset outboard securement 160 in the front waistband portion of the article may be positioned laterally inboard or outboard of its corresponding adjacent perimeter bond 130. Desirably, the outboard securement 160 in the front waistband portion is located laterally outboard of its corresponding perimeter bond 130. In other desired configurations, the outboard securement 160 in the front waistband portion can be placed in the proximity of the gusset-flap outboard side edge 152. Another arrangement can have the outboard securement 160 connected to its corresponding perimeter bond 130 with an additional bond segment, but this additional bond segment should be configured so that this additional bond does not cut or otherwise deactivate the elastomeric members 138 in a manner which reduces the desired, effective free elastic length in the leg gusset portion of the gusset-flap 19.

Each leg gusset outboard securement 160 in the back waistband portion of the article may be placed laterally inboard or outboard of its correspondingly adjacent perimeter bond 130. In particular aspects, the outboard securement 160 in the back waistband portion is positioned laterally outboard of its corresponding perimeter bond 130, as representatively shown in FIG. 16. In desired arrangements, the outboard securement 160 in the back waistband portion can be located in the proximity of the gusset-flap edge 152. In other arrangements, the outboard securement 160 in the back waistband portion may be connected to its corresponding perimeter bond 130 with an additional bond segment, but this additional bond segment should be configured such that this additional bond does not cut or otherwise deactivate the elastomeric members 138 in a manner which reduces the desired, effective free elastic length in the leg gusset portion of the gusset-flap 19.

In particular aspects, the perimeter bond attachment 130 may terminate laterally inboard from and longitudinally even with the juncture region 52, particularly the intersection point at which its corresponding side edge contour 15 crosses the outboard side edge 152 of its corresponding leg gusset section. This placement of the intermediate region perimeter bond 130 can give an advantageous combination of providing a seal in the article intermediate portion 16, avoiding the area of the absorbent body 32, and allowing the leg gusset section 142 to maintain the desired conformance against the wearer.

In other aspects, the perimeter bond attachment 130 can be positioned inboard from the intersection point of its corresponding juncture region 52, and can extend longitudinally past and away from the intersection point by an appointed inset distance 154 of not more than a maximum of about 80 mm. Alternatively, the inset distance can be not more than about 60 mm, and optionally, can be not more than about 40 mm to provide improved performance. Other desired configurations can include an inset distance of not more than about 20 mm. An effective limit to the extension of the perimeter bond beyond the juncture region 52 may be the point at which the perimeter bond would intersect the absorbent body 32. In desired aspects, the perimeter bond 130 is configured to substantially avoid extending over the area of the absorbent body 32, particularly the retention portion 48 to prevent excessive leakage. If the absorbent pad 32 is shaped in such that a continuation of the perimeter bond 130 substantially avoids intersecting the absorbent body 32, another effective limit for the length of the perimeter bond 130 may be the front waistband edge of the article. For example, the perimeter bond 130 may include a straight line segment which extends to approximately the longitudinally terminal edge 94 of the article, the straight line segment would not cross over the absorbent body.

Each leg gusset section 142 can have an effective lateral width 186 (e.g. FIG. 6), and the lateral gusset width 186 is desirably greater than a lateral width 58 of its corresponding containment flap section 144. To provide improved independence of the movement of the outboard edge 152 of the leg gusset section 142, the perimeter bond 130 is spaced along the cross dimension 24 in a direction laterally inboard from the outboard edge 152 of its corresponding leg gusset section 142 by a perimeter bond spacing distance 128 (e.g. FIGS. 6 and 16) which is at least a minimum of about 15 mm. Alternatively, the perimeter bond spacing distance 128 can be at least about 20 mm, and optionally, can be at least about 25 mm to provide improved performance. If the perimeter bond spacing distance is too small, the leg gusset section 142 can be less able to conform closely to the body of the wearer, and may leave excessive gaps during use.

In further aspects of the invention, each leg gusset section 142 can have perimeter bond spacing distance 128 which is not more than about 104 mm (e.g. FIG. 6). The lateral width of the leg gusset section can alternatively be not more than about 76 mm, and optionally can be not more than about 51 mm. Additionally, particular aspects of the invention can be configured with each leg gusset section having a perimeter bond spacing distance 128 which is greater than a lateral width 58 of its corresponding containment flap section 144.

In additional aspects, the desired perimeter bond spacing distance 128 can be maintained along a selected portion of the longitudinal article length 180. In particular configurations, the selected minimum spacing distance 128 between said perimeter bond attachment 130 and the outboard side edge 152 of the leg gusset section can be substantially maintained with respect to a substantially continuous, distance of at least about 3 cm along the article longitudinal direction 26. Alternatively, this substantially continuous, longitudinal distance can be at least about 5 cm, and optionally, can be at least about 10 cm to provide improved fit and leakage protection.

In other aspects, the perimeter bond spacing distance 128 between the perimeter bond attachment 130 and the outboard side edge 152 of the leg gusset section can be maintained at the appointed minimum value along a substantially continuous longitudinal distance which is approximately equal to the length of the perimeter bond 130. In particular configurations, the perimeter bond spacing distance 128 can be maintained at the appointed minimum value with respect to a substantially continuous, distance of at least 20% of the longitudinal article length 180. Alternatively, the spacing distance 128 can be maintained along a substantially continuous, longitudinal distance of at least about 30% of the longitudinal article length 180, and optionally, can be maintained along a substantially continuous longitudinal distance of at least about 40% of the article length 180 to provide improved performance. If the longitudinal distance of the maintained perimeter bond spacing distance is too short, there can be insufficient control of the leg gusset section.

The perimeter bond attachment 130 can advantageously be constructed to provide an operative seal against leakage of liquid between the gusset-flap member 19 and the topsheet 28, and between the topsheet 28 and backsheet 30 along at least a significant longitudinal length of the intermediate portion 16 of the article. In particular aspects, the seal length can be at least about 2.5 cm. Alternatively the seal length can be at least about 5 cm, and optionally, can be at least about 10 cm to provide improved leakage resistance. In particular aspects, the seal length can be at least about 20% of longitudinal length 180. Alternatively the seal length can be at least about 30% of longitudinal length 180, and optionally, can be at least about 40% of longitudinal length 180 to provide improved leakage resistance.

Figure 17:
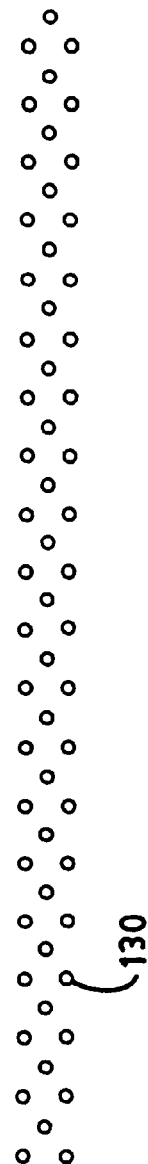
FIG. 17 representatively shows a dot bond pattern which may be employed with the present invention.
Figure 17A:
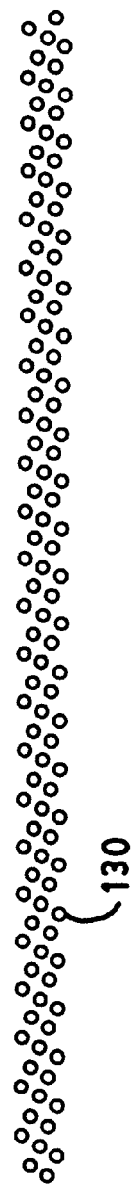
FIG. 17A representatively shows another dot bond pattern which may be employed with the present invention.
Figure 17B:
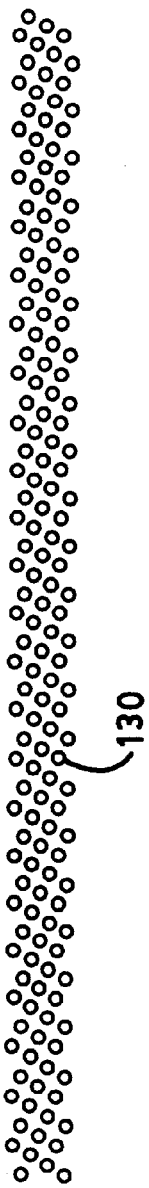
FIG. 17B representatively shows still another dot bond pattern which may be employed with the present invention.

The operative seal of the perimeter bond attachment 130 can also be improved by controlling the density and type of the attachment pattern. For example, the perimeter bond 130 may provide a substantially continuous seal. Another arrangement may include ultrasonic bonding to form the perimeter bond 130, and the ultrasonic bonding may include dot patterns of various densities, such as representatively shown in FIGS. 17 through 17B. The dot patterns can be packed closer together to provide a more tortuous path which has a greater resistance to leakage. Alternatively, the dot bonds may be replaced with other shapes, such as rods, lines, s-shapes, zig-zags and the like, as well as combinations thereof. Additionally, other conventional methods may be employed to provide the operative tortuous path which sufficiently prevents liquids from leaking past the side edges of the article.

In the various aspects of the invention, the perimeter bond attachments 130, and the leg gusset outboard securements 160 can allow the outboard edge 152 of the leg gusset section 142 to act substantially independently from the backsheet and topsheet layers, particularly at the juncture regions 52 where each of the waistband portions 12 and 14 transitions into the intermediate portion 16 of the article, and where the overlapping portion of the outboard edge 152 of each leg gusset section 142 is superposed with at least the backsheet layer 30. The resultant construction can provide better conformance of the leg gusset section 142 to the wearer's body.

In particular aspects of the invention, the gusset outboard securement 160 in the front waistband portion 12 of the article can extend from approximately the front waistband edge 94 of the article to approximately the location of its corresponding juncture region 52 of the article, and particularly the intersection point of the juncture region. In other aspects of the invention, the gusset outboard securement 160 may extend from approximately the front waistband edge 94 to a terminal location which stops short of and is longitudinally spaced away from the juncture region 52, particularly the intersection point of the juncture region, by a distance of not more about 40 mm. Alternatively, the gusset outboard securement 160 can extend from approximately the front waistband edge 94 to a location which is longitudinally spaced away from its corresponding juncture region 52 by a distance which is not more than about 30 mm, and optionally, is not more than about 20 mm.

In other aspects, the gusset outboard securement 160 in the back waistband portion 14 of the article can extend from approximately the back waistband terminal edge 94 of the article to approximately the location of its corresponding juncture region 52 of the article, particularly the intersection point of the juncture region. In other aspects of the invention, the gusset outboard securement 160 may extend from approximately the back waistband edge 94 to a terminal location which stops short of and is longitudinally spaced away from its corresponding juncture region 52, particularly the intersection point of the juncture region, by a distance of not more about 40 mm. Alternatively, the gusset outboard securement 160 can extend from approximately the back waistband edge 94 to a location which is longitudinally spaced away from the juncture region 52 by a distance which is not more than about 30 mm, and optionally, is not more than about 20 mm.

As mentioned previously, it can be desirable to place gusset outboard securements 160 at or near leg gusset outboard edge 152. The outboard securements 160 may, for example, include an adhesive, such as a hot melt adhesive or the like. The outboard securements may, for example, be employed in conjunction with additional securements, such as adhesive bonds, which further attach the area of the leg gusset end portions 137 to the absorbent article. To further improve performance of the absorbent article, the outboard edge 152 of the leg gusset section 142 can be substantially unattached to the article along a free-edge length 162 of at least about 14 cm (e.g. FIG. 16). The free-edge length can alternatively be at least about 16 cm, and optionally can be at least about 30 cm to further improve performance. In other aspects, the free-edge length 162 can be not more than about 45 cm. Alternatively, the free-edge length can be not more than about 40 cm, and optionally, the free-edge length can be not more than about 35 cm to provide improved benefits.

In additional aspects, the outboard edge 152 of the leg gusset section 142 can be substantially unattached to the article along a free-edge length 162 which is at least about 44% of an overall length of the article. The free-edge length can alternatively be at least about 52% of the overall length of the article, and optionally can be at least about 60% of the overall length of the article to provide improved performance. In some aspects of the invention, the free edge length 162 can be substantially equivalent to the longitudinal length 180, but this is not as desirable as some other embodiments due to curling of waist areas on the wearer. In still other aspects, the free-edge length 162 can be not more than about 90% of the overall length of the article. Alternatively, the free-edge length can be not more than about 80% of the overall length of the article to provide further improved benefits.

The perimeter bond 130 may extend through the complete longitudinal length of the diaper 10. The perimeter bond 130 may optionally be configured to not extend over the complete length of the overlap of the gusset section 142 with the terminal, side edge margins of the topsheet and backsheet layers which corresponds to each of the gusset sections 142.

In particular aspects, the gusset perimeter bond 130 has a longitudinal extent 132 of not more than about 90% of the total, overall length 180 of the article. The longitudinal extent 132 of the gusset perimeter bond can alternatively be not more than about 80%, and optionally can be not more than about 60% of the length of the article. As a result, a portion of either or both of the longitudinal end portions 150 of each gusset section 142 can move substantially independently its immediately adjacent portions of side margin of the topsheet and backsheet layers, while also causing the side margins of the topsheet and backsheet layers within the crotch section of article to move in a substantial correspondence and compliance with the portion of the gusset section 142 located in the crotch section.

The gusset perimeter bond 130 can be a substantially continuous bond, or may alternatively be a discontinuous bond composed of a regular or irregular pattern of attachments. In the illustrated configuration, for example, the gusset perimeter bond can be provided by a selected pattern of discrete sonic bonds which are distributed over a selected bonding area. The bonding area can have a lateral width which is at least about 0.2 cm, and alternatively is at least about 1 cm. In other aspects the lateral width of the bonding area can be up to about 8 cm, and optionally, can be up to about 15 cm to provide improved performance. The gusset perimeter bond can be substantially straight, or can be curved to substantially follow the terminal edges of the topsheet and/or backsheet layers. In addition, the laterally outboard edge of at least a portion of the perimeter bond 130, particularly within the crotch region of the article, can be substantially coterminous with the laterally terminal edges of the topsheet and/or backsheet layers to provide improved aesthetics and performance.

The perimeter bond 130, the leg gusset outboard securement 160, the flap distal securement 79, and any other supplemental securements which extend therebetween may be provided by any operative securing mechanism. For example, the securing mechanism may include ultrasonic bonding, thermal bonding, mechanical embossing, thermal embossing, pin aperturing, adhesive bonding and the like, as well as combinations thereof.

Each leg gusset section 142 can include a first arrangement of a first plurality of two or more separate, longitudinally extending elastomeric members 138 which are laterally spaced outboard from the side edge contour 15 of the backsheet layer 30 by a discrete distance, at least within the crotch region 18 of the article. In desired arrangements, the laterally spaced elastomeric members substantially avoid having a lamination onto or other direct or immediate connection to the backsheet layer 30 and thereby substantially avoid providing a direct gathering of the backsheet layer, at least within the crotch region 18 of the article.

In particular aspects of the invention, the leg gusset section 142 can have a composite stiffness which is not less than about 5 mg. The composite stiffness can alternatively be not less than about 10 mg, and optionally can be not less than about 15 mg. In other aspects of the invention, the leg gusset section 142 can have a composite stiffness which is not more than about 250 mg. The composite stiffness can alternatively be not more than about 200 mg, and optionally can be not more than about 170 mg.

The stiffnesses of the various components and sections of the article of the invention can be determined by employing the test methodology of TAPPI T543 om-94, and by employing a Gurley Digital Stiffness tester, Model 4171-D, a device available from Teledyne Gurley, a business having offices located in Troy, N.Y. Accordingly, the stiffness values of the various sections of the article, such as the waist pocket member 80, are bending stiffnesses. The stiffnesses can be expressed as milligrams (mg) which correspond to milligrams-force, or may be expressed in terms of the numerically equivalent values of Standard Gurley Units (SGU). For the purposes of the present invention, the axis about which a bending moment is applied to the sample during the stiffness testing is a bending axis which is aligned substantially parallel to the direction of elastic stretch and gathering provided by the associated elastic members, such as elastic members 138 and/or 68. For example, the stiffness of the leg gusset section 142 is taken with respect to the cross-dimension of the article. The stiffness is determined with respect to a bending moment which is applied about a bending axis that is generally aligned along the longitudinal dimension 26 of the article. A suitable device for taking the stiffness measurements is a Gurley Digital Stiffness tester, Model 4171-D, available from Teledyne Gurley, a business having offices in Troy, N.Y.; or an equivalent device. A suitable testing procedure is TAPPI T543 om-94.

Figure 14:
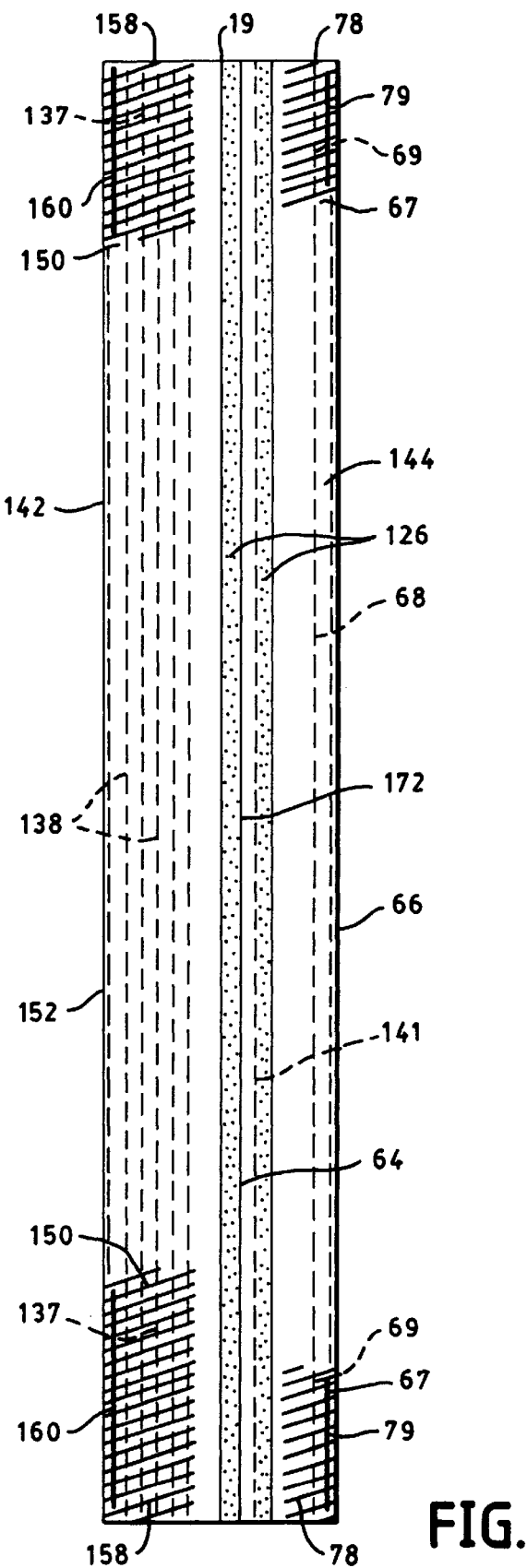
FIG. 14 representatively shows a schematic, top view of the gusset-flap member and its construction.
Figure 15:
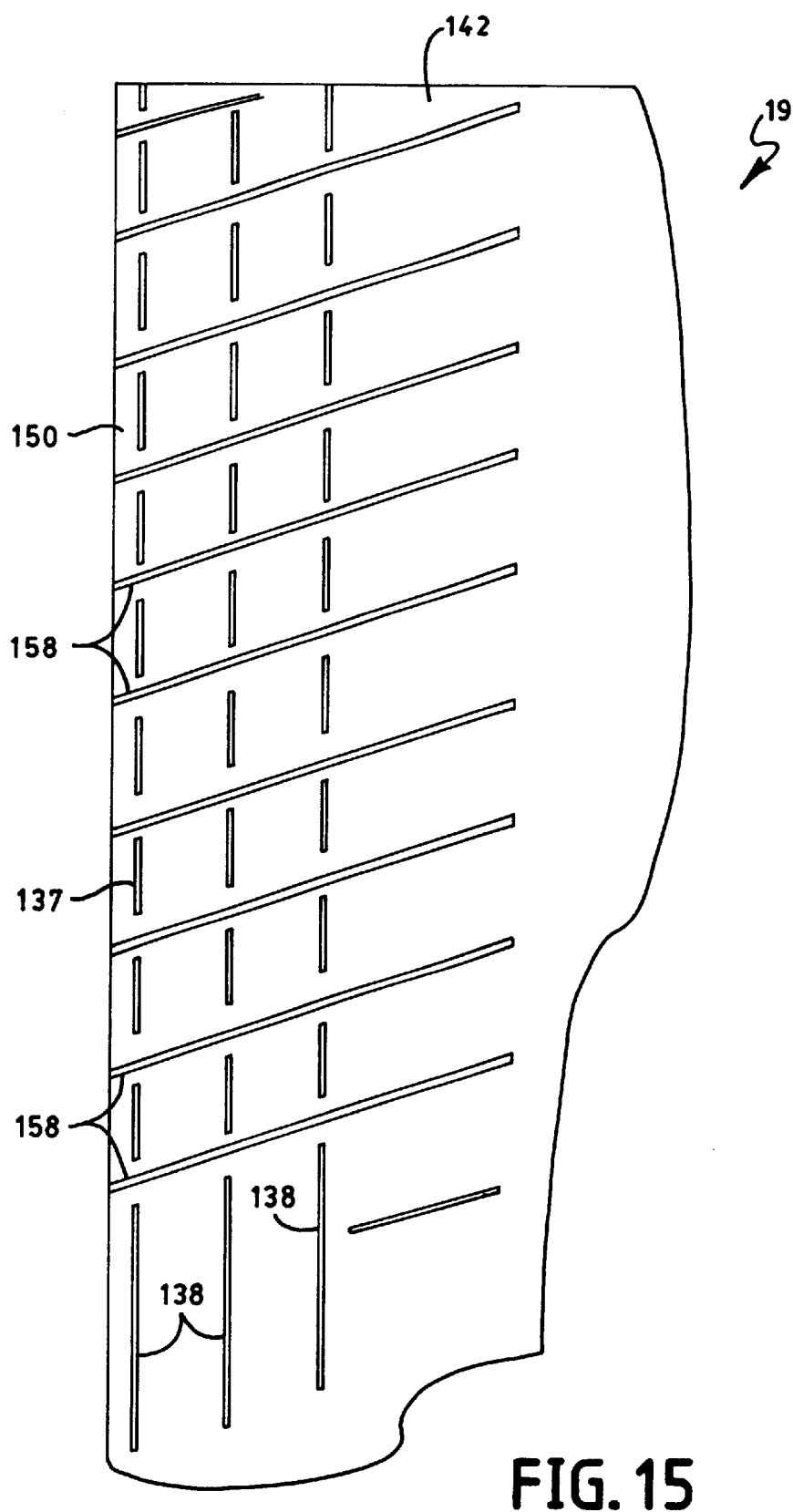
FIG. 15 representatively shows a schematic view of a deadening pattern in the leg gusset portion of the gusset-flap member.
Figure 16:
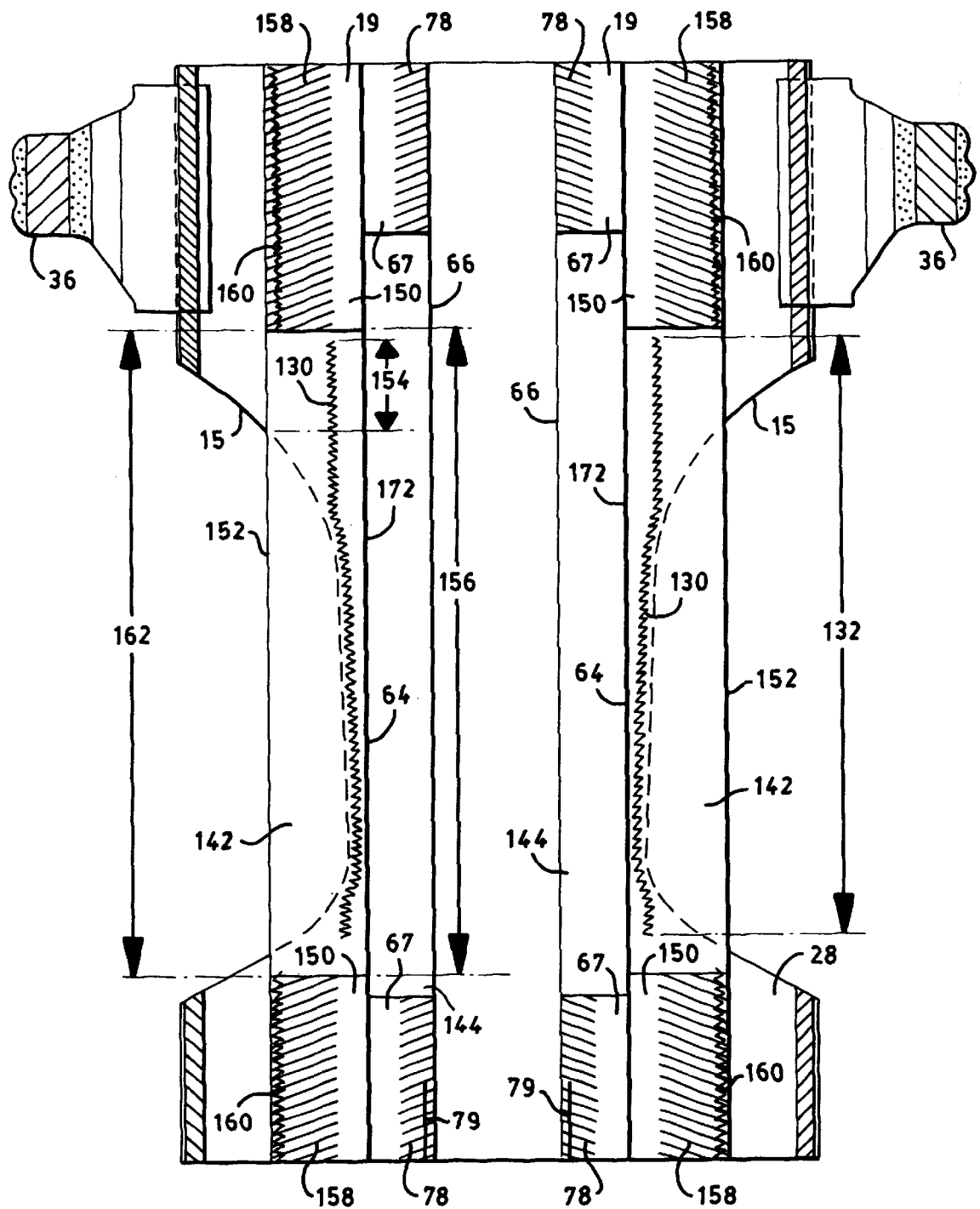
FIG. 16 representatively shows a schematic top view of the article of the invention showing the gusset-flap members and another arrangement of the perimeter bond attachments along the side contours of the article.

With reference to FIGS. 14, 15 and 16, the article of the invention can include at least one end portion 137 of the first arrangement of elastomeric members 138 in the leg gusset section 142 which is substantially deactivated to provide at least one gusset end portion 150 of each leg gusset section 142 which is substantially non-gathered along the longitudinal direction 26. Desirably, each end portion 137 of the first arrangement of elastomeric members 138 in each leg gusset section 142 is substantially deactivated. In particular arrangements, an outboard deadening array 158 can be employed to deactivate the appointed end portion of the first arrangement of elastomeric members.

The end portion 137 of the first arrangement of elastomeric members 138 can, for example, be deactivated at a first plurality of longitudinally spaced apart locations to provide the at least one gusset end portion of each leg gusset section which is substantially non-gathered. In particular aspects, the deactivation of the end portion of the first arrangement of elastomeric members may include a segmenting of the end portion of the first arrangement of elastomeric members 138 at the first plurality of longitudinally spaced apart locations to provide the at least one gusset end portion of each leg gusset section which is substantially non-gathered. It should be readily appreciated that the above-mentioned segmenting may be accomplished by any of a variety of conventional techniques, such as cutting, melting or the like, as well as combinations thereof.

It should also be recognized that the configuration of the deadening array 158, which segments the appointed end portion 137 of the first arrangement of elastomeric members 138, does not need to cut or otherwise segment the elastomeric members 138 at every one of the plurality of spaced apart locations. At some of the spaced apart locations, the elastomeric members may remain unsegmented by the deactivation pattern, but may nonetheless have their elastomeric properties effectively deadened and rendered inoperative.

In addition to the discrete segmenting of the elastomeric members 138 at the appointed plurality of spaced apart locations, the leg gusset outboard deadening array 158 may be configured to provide a leg gusset flat zone area. In the flat zone area, the elastomeric members 138 (and associated components) can, for example, be ironed or otherwise flattened without cutting or segmenting, to thereby effectively deactivating the elastomeric members in the flat zone portion of the leg gusset, outboard deadening array 158.

A suitable technique for deactivating the first arrangement of elastomeric members 138 at the end portion of leg gusset section can include the deadening array 158 provided by the pattern of sonic bonds representatively shown in FIG. 15. In desired configurations, the sonic bonds can help attach the at least one gusset end portion 150 of each leg gusset section 142 to the article, and can also deactivate the end portion of the first arrangement of elastomeric members by overheating the elastic members and/or by cutting the elastomeric members. Suitable techniques for deactivating the elastomeric members can include thermal bonding techniques, sonic bonding techniques, adhesive bonding techniques, a disabling of adhesive bonds between the elastic members and the fabric material of the leg gusset section, an application of a hot polymer or polymer blend in a set pattern to deactivate the strands, or the like, as well as combinations thereof. Optionally, the elastomeric members can effectively be deactivated at the end portions 150 of the leg gusset section by not operatively attaching the elastomeric members to the constituent layer materials at the end portions of the leg gusset section. As a result, any contraction of the elastomeric members would be unable to gather the layer materials at those end portions.

The article can additionally include a leg gusset, outboard securement 160 which attaches at least one gusset end portion 150 of each leg gusset section 142 to the article. Desirably, each gusset end portion 150 of each leg gusset section 142 is attached to the article with a corresponding outboard securement. Optionally, the leg gusset outboard securement 160 may also operatively deactivate the end portion of the first arrangement of elastomeric members.

Still other aspects of the invention may form the leg gusset outboard securement 160 in a configuration which attaches the leg gusset section 142 to the article at a plurality of longitudinally spaced apart locations, and also deactivates (e.g. segments) the end portion 137 of the first arrangement of elastomeric members 138 at the plurality of longitudinally spaced apart locations to thereby provide the at least one gusset end portion 150 of each leg gusset section 142 which is substantially non-gathered.

The various configurations of the gusset-flaps 19 can advantageously include elasticized, barrier flaps, such as the illustrated containment flap sections 144 at the legband regions of the diaper. The shown configurations, for example, include two containment flap sections 144 which are operably connected to extend above and over the bodyside surface of the topsheet layer 28. Alternative, constructions and arrangements for the containment flap sections 144 are, for example, described in U.S. Pat. 4,704,116 issued Nov. 3, 1987, to K. Enloe, the disclosure of which is hereby incorporated by reference in a manner that is consistent (not contradictory) herewith. Other alternative configurations of the containment flap sections 144 are described in U.S. Pat. No. 5,562,650 entitled ABSORBENT ARTICLE HAVING AN IMPROVED SURGE MANAGEMENT which issued Oct. 8, 1996 to R. Everett et al., the disclosure of which is hereby incorporated by reference in a manner that is consistent herewith.

The containment flap sections 144 can be attached to the topsheet layer 28 along length-wise extending fixed regions, such as fixed edges 64, of the flap sections. A movable edge 66 of each containment flap section includes a selected, second arrangement of flap elastic member 68 which can comprise one or more individual strands of elastomeric material. For example, a plurality of elastic strands may be configured in a spatially separated, generally parallel arrangement, and a suitable elastic strand can, for example, be composed of a 470 decitex LYCRA elastomer which is available from E.I. DuPont de Nemours, a business having offices in Wilmington, Del. Alternatively, the elastic strands may be composed of 700 denier GLOSPAN S7 spandex elastomer which is available from Globe Manufacturing, a business having offices in Fall River, Mass.

Each elastic member 68 is connected to the movable edge region of the containment flap section 144 in an elastically contractible condition such that the contraction of the elastic components thereof gathers and shortens the edge of the containment flap section. As a result, the movable edge of each containment flap section tends to position itself in a spaced relation away from the bodyside surfaces of topsheet 28 and/or surge management portion 46 toward a generally upright and approximately perpendicular configuration, especially in the crotch section 18 of the diaper. In the shown embodiment, for example, the moveable edge of the containment flap section is operatively connected to the flap elastics by partially folding or otherwise doubling the flap material back upon itself by a limited amount which is sufficient to enclose the selected arrangement of the elastics 68 located in the flap section 144. More particularly, the inboard side portion 62 of the fabric layer can be folded or otherwise wrapped around an appointed second folding line 189. The elastomeric members 68 can then be sandwiched or otherwise contained between two laminations of the fabric 176. In addition, the inboard side portion 62 of fabric layer and the primary, base portion of the containment flap section 63 of the fabric layer can be substantially unattached to each other at intermediate regions 90 located between immediately adjacent members of the first plurality of elastomeric members 138. For example, each elastic member of the first plurality of elastomeric members 68 in each of the containment flap sections 144 can be attached to its corresponding portions of the fabric layer 176 with a substantially separate strip of adhesive. The individual, spatially separated adhesive strips substantially avoid touching one another. As a result, the substantially unattached intermediate regions 90 can blouse and more effectively form a cushioning topography.

In other arrangements of the invention, an adhesive spray can be configured to concentrate the adhesive spray at the positions of the elastic members 68 while depositing minimal amounts of adhesive is in the spaces 90 between the elastic members 68, in the space 164 separating the containment flap elastics 68 from the leg gusset elastics 138, and/or in the folding line area 189. While there may or may not be a discrete spacing between the areas of applied adhesive in this particular arrangement, it has been noted that this arrangement provides sufficient adhesive bonding without unduly stiffening the containment flap portion of the gusset-flap composite. This arrangement can also help form a more cushioning topography in the containment flap portion of the gusset-flap.

At least a pair of the containment, barrier flap sections 144 are connected and disposed along laterally opposed, longitudinally extending regions of topsheet layer 28, and the connected topsheet regions are located generally adjacent to laterally opposed side edge regions of the medial section of topsheet layer 28. The connected topsheet regions are located substantially laterally inboard of the leg gusset sections 142 of the diaper article 10, but portions of the connected regions of the topsheet may optionally be located outboard of the leg gusset sections.

Each containment flap section 144 includes at least one of the elastomeric members 68 attached to the containment flap section at a location which is proximate to the movable edge 66 of the containment flap section. In particular configurations, at least one of the elastomeric members 68 is attached to the containment flap section at a location which is proximate to the substantially fixed edge 64 of the containment flap section.

With reference to FIG. 6, each containment flap section 144 may include one or more elastomeric members with at least one base elastomeric member 68a which is attached to the containment flap section 144 at a location which is between the movable edge portion 66 and the substantially fixed edge 64 of the containment flap section. In particular configurations, the base elastomeric member 68a can be attached to the containment flap section 144 at a location which is proximate the movable edge portion 66 of the containment flap section. The base elastic member may have a spacing distance 166 with an upper bound which is not more than about 37 mm from the fixed edge 64 of the containment flap section, at least within the crotch portion 18 of the article. In particular arrangements, the at least one base elastomeric member can be attached substantially immediately adjacent to the fixed edge 64 of the containment flap section 144.

In particular aspects of the invention, adjacent elastomeric members 68 can have a spacing distance 60 which is not less than about 2 mm. The spacing distance between the adjacent elastomeric members 68 can alternatively be not less than about 2 mm, and optionally can be not less than about 4 mm. In other aspects, the adjacent elastomeric members 68 can have a spacing distance 60 which is not more than about 25 mm. The spacing distance between adjacent elastomeric members 68 can alternatively be not more than about 13 mm, and optionally can be not more than about 8 mm to provide desired effectiveness.

In desired arrangements, each containment flap section 144 can have a lateral width dimension 58 (FIG. 6) of at least about 13 mm, and in particular aspects of the invention, the containment flap width is less than the effective width 186 of its corresponding leg gusset section 142. Additionally, each containment flap section 144 may have a longitudinal length which is substantially equal to the overall, total length 180 (FIG. 1) of the article. Alternatively, each containment flap section may have a length which is less than the overall, total length of the article, and the shorter containment flap section may be configured with a zoned-placement at a selected location along an appointed portion of the overall length of the article. For example, the length of the containment flap section may be substantially centrally located along the article length, or may be positioned with an offset toward the front or back waistband of the article. Optionally, each containment flap section may have a length which is substantially equal to or less than the overall, total length of the absorbent body structure 32, and the relatively shorter containment flap section may be configured with a zoned-placement at a selected location along an appointed portion of the overall length of the absorbent body structure.

The containment flap sections 144 are operably secured to appointed sections of the article, such as laterally opposed sections of the topsheet layer 28, with a suitable attachment mechanism. In particular arrangements, for example, the containment flap attachments can be similar to those employed with the waist pocket member 80. The attachments can have a generally U-shape configuration, with the bottom of the U-shape extending generally longitudinally and the two arms of the U-shape extending generally laterally. The shown U-shape is angular, but may be non-angular, if desired. As illustrated in the shown arrangements, the flap attachments can be operatively combined and integrated with the leg gusset attachments 172. Alternatively, the flap attachments can be distinct and separate from the leg gusset attachments, if desired.

With reference to FIGS. 14, 15 and 16, the article can further include at least one end portion 69 of the second arrangement of at least one elastomeric member 68 in the containment flap section 144 which is substantially deactivated to provide at least one flap end portion of each containment flap section which is substantially non-gathered along the longitudinal direction 26. Desirably, each end portion 69 of the second arrangement of at least one elastomeric member in each containment flap section 144 is substantially deactivated. In particular arrangements, a distal deadening array 78 can be employed to deactivate the appointed end portion of the second arrangement of elastomeric members.

The end portion 69 of the second arrangement of the at least one elastomeric member 68 can be deactivated at a second plurality of longitudinally spaced apart locations to provide the at least one flap end portion of each containment flap section which is substantially non-gathered. In particular aspects, the desired deactivation of the end portion 69 of the second arrangement of elastomeric members 68 may include a segmenting of the end portion of the second arrangement of elastomeric members at the second plurality of longitudinally spaced apart locations to provide the at least one substantially non-gathered, flap end portion of each containment flap section. It should be readily appreciated that the above-mentioned segmenting may be accomplished by any of a variety of conventional techniques, such as cutting, melting or the like, as well as combinations thereof.

It should also be recognized that the configuration of the deadening array 78, which segments the appointed end portion 69 of the second arrangement of elastomeric members 68, does not need to cut or otherwise segment the elastomeric members 68 at every one of the second plurality of spaced apart locations. At some of the spaced apart locations, the elastomeric members may remain unsegmented by the deactivation pattern, but may nonetheless have their elastomeric properties effectively deadened and rendered inoperative.

In addition to the discrete segmenting of the elastomeric members 138 at the appointed plurality of spaced apart locations, the leg gusset outboard deadening array 158 may be configured to provide a leg gusset flat zone area. In the flat zone area, the elastomeric members 138 (and associated components) can, for example, be ironed or otherwise flattened without cutting or segmenting, to thereby effectively deactivating the elastomeric members in the flat zone portion of the leg gusset, outboard deadening array 158.

An example of a suitable technique and configuration for deactivating the second arrangement of elastomeric members 68 at the end portion 67 of containment flap section 144 is the pattern array of sonic bonds schematically shown in FIG. 15 for deactivating the elastomeric members 138 at the end portion 137 of the leg gusset section 142. In desired configurations, the sonic bonds can attach the at least one containment flap end portion 67 of each containment flap section 144 to the article, and can also deactivate the end portion of the second arrangement of elastomeric members 68 by overheating the elastic members and/or by cutting the elastomeric members. Other suitable techniques for deactivating the elastomeric members can include thermal bonding techniques, sonic bonding techniques, adhesive bonding techniques, a disabling of adhesive bonds between the elastic members and the fabric material of the containment flap section, an application of a hot polymer or polymer blend in a set pattern to deactivate the strands, or the like, as well as combinations thereof. Optionally, the elastomeric members can effectively be deactivated at the end portions 67 of the containment flap section by not operatively attaching the elastomeric members to the constituent layer materials at the end portions of the containment flap section. As a result, any contraction of the elastomeric members would be unable to gather the layer materials at those end portions.

The article can additionally include a containment flap, distal securement 79 which attaches at least one flap end portion 67 of each containment flap section 144 to the article. Desirably, each flap end portion 67 of each containment flap section 144 is attached to the article with a corresponding distal securement. Optionally, the containment flap distal securement 79 may also operatively deactivate the end portion 69 of the second arrangement of elastomeric members 68.

Still other aspects of the invention may form the containment flap, distal securement 79 in a configuration which attaches the containment flap section 144 to the article at the second plurality of longitudinally spaced apart locations, and also deactivates (e.g. segments) the end portion 69 of said second arrangement of elastomeric members 68 at the second plurality of longitudinally spaced apart locations to thereby provide the at least one flap end portion of each containment flap section which is substantially non-gathered.

With reference to FIG. 6, a further aspect of the invention can have an optional configuration wherein the barrier layer 174 is extended into the containment flap section 144 of each leg-gusset 19. As a result, the relatively inboard, second side edge 141 of the barrier layer 174 is located within the containment flap section 144. With this arrangement, the inboard portion 62 of the fabric layer 176 extends beyond and past the corresponding, longitudinally extending, second side edge 141 of the barrier layer. The fabric side portion 62 is appointed for folding and wrapping about its appointed, second folding line or region 189 to extend across and over at least the portion the second major surface 149 which is located in the containment flap section 144. Accordingly, the relative arrangements of the barrier layer region 61, the fabric layer region 63 and the second array of elastomeric members 68 within the containment flap sections 144 can be similar to the arrangements of the similar components provided in the leg gusset sections 142. For example, the fabric side portion 62 can overlie a substantial entirety of the second major surface 149 of the barrier layer region 61 in the flap section 144, and can substantially completely cover the second major surface of the portion of the barrier layer which is located in the containment flap section 144. Accordingly, the fabric side portion 62 can be interposed between the barrier layer and the wearer's skin.

The arrangement or array of elastomeric members 68 in each containment flap section 144 can be attached to at least one of the barrier and fabric layer regions 61 and 63, respectively, with a suitable securing mechanism, such as a selected pattern of adhesive or other type of bonding. For example, the adhesive may be applied by spraying adhesive discontinuous droplets or filaments, and/or may be applied by arranging generally continuous lines of adhesive in a selected pattern, such as a swirl pattern. Alternatively, the hot melt spray pattern may be concentrated in the vicinity of the elastomeric members, although a limited, reduced amount of adhesive may be in the interstitial spaces between the elastomeric members. Alternatively, the elastomeric members 68 can be attached to at least one of the barrier and fabric layers with a plurality of individual, longitudinally extending strips of adhesive. Each individual adhesive strip is spatially separated from immediately adjacent adhesive strips by a discrete distance, and each individual adhesive strip is arranged to attach substantially an individual one of the elastomeric members 68 to the at least one of the barrier and fabric layers. In the shown arrangements, for example, the strips of adhesive can be aligned substantially parallel to one another.

In a particular aspect of the invention, the fabric layer 176 and the barrier layer in the containment flap section 144 are substantially unattached to each other at intermediate regions 90 (FIG. 6) located between immediately adjacent members of the second plurality of elastomeric members 68. In another aspect of the invention, each elastic member of the second plurality of elastomeric members 68 of the containment flap sections 144 can be attached to at least one of the flap region 61 of the barrier layer and/or the containment flap regions of the fabric layer 176 with a substantially separate strip of adhesive in a manner similar to that employed in the construction of the leg gusset section 142. Accordingly, the individual, spatially separated adhesive strips substantially avoid touching one another, and the substantially unattached intermediate regions 90 can blouse and more effectively form a cushioning topography.

In another aspect of the invention, the fabric layer 176 and the barrier layer in the containment flap section 144 may be lightly attached with hot melt adhesive at the intermediate regions 90 located between immediately adjacent members of the second plurality of elastomeric members 68, but with the bulk of the hot melt adhesive concentrated at the locations of the elastomeric members 68. In another aspect of the invention, each elastic member of the second plurality of elastomeric members 68 of the containment flap sections 144 can be attached to at least one of the flap regions 61 of the barrier layer and/or the containment flap regions of the fabric layer 176 with a heavier concentration of adhesive 74 at the elastomeric members 68 in a manner similar to that employed in the construction of the leg gusset section 142. Accordingly, the lightly attached intermediate regions 90 can more readily blouse and more effectively form a cushioning topography.

All of the elastomeric members 68 can be attached on one single surface of the containment flap region 61 of the barrier layer. For example, all of the elastomeric members 68 can be attached on the first major surface 148 and covered by the primary, base portion of the containment flap region 63 of the fabric layer (FIG. 7). Alternatively, all of the elastomeric members 68 can be attached on the second major surface 149 and covered by the inboard side portion 62 of the fabric layer (FIG. 8).

The second arrangement elastomeric members 68 may also include a second a first sub-set of individual elastomeric members joined to the first major surface 148 of the barrier layer 174, and a second sub-set of individual elastomeric members joined to the second major surface 149 of the barrier layer (FIGS. 4 and 6). In addition, the first and second sub-sets of elastomeric members can be arranged in a laterally offset and staggered configuration.

In other arrangements of the invention, the elastic members 68 in the containment flap section 144 can be spaced from the closest elastic members 138 in the gusset section 142 by a predetermined boundary space 164 (FIG. 6) which provides a minimum separation distance of at least about 2 mm. In particular aspects, the separation distance provided by the boundary spacing distance is at least about 8 mm, and optionally is at least about 16 mm. The separation distance provides an amount of isolation which effectively permits the containment flap elastic members 68 to operate substantially separately from the gusset elastic members 138. Accordingly, the gathering provided by the containment flap elastics can be substantially separated from the gathering provided by the gusset elastics.

In particular aspects of the invention, each containment flap section 144 has a composite stiffness of at least about 5 mg, taken with respect to the cross dimension of the article. For the purpose of the present invention, the stiffness of the containment flap section is determined with respect to a bending moment which is applied about a bending axis that is substantially aligned along the longitudinal dimension 26 of the article. Desirably, the containment flap section has a composite stiffness which is not less than about 10 mg, and alternatively, is not less than about 15 mg to provide improved containment. In further aspects, the containment flap section can have a composite stiffness which is not more than about 250 mg. The composite stiffness can alternatively be not more than about 200 mg, and optionally can be not more than about 170 mg to provide desired performance. If the stiffness of the containment flap section 144 is too low, the containment flap section may excessively collapse upon itself. If the stiffness of the containment flap section is too high, there may be excessive irritation of the wearer's skin.

As representatively shown, the article of the invention can be configured with each gusset-flap 19 connected directly or indirectly to an inwardly facing, appointed bodyside surface of the topsheet layer 28. Each gusset-flap member 19 can have a longitudinal length thereof which (as an approximate lower bound) extends along at least about 20 percent of the total longitudinal length 180 (FIG. 1) of the article. In other configurations, each gusset-flap member 19 can extend along at least about 30 percent, and alternatively at least about 40 percent of the longitudinal length 180 of the article to provide improved effectiveness. As illustrated in the representatively shown configurations, each gusset-flap member can extend along a longitudinal length which (as an approximate upper bound) can be up to about 100 percent of the total longitudinal length of the article to provide further gasketing and containment. Alternatively, each gusset-flap member can extend along a length which is not more than about 80 percent, and optionally is not more than about 70 percent of the total longitudinal length of the article to provide desired performance.

Each gusset section 142 of the gusset-flap 19 can be in a bridging configuration across its associated, concave side edge contour 15 of the backsheet layer along a length 182 which is at least about 20 percent of the longitudinal length 180 of the article. In other configurations, each gusset section can be in a bridging configuration across its associated, concave side edge contour 15 of the backsheet layer along a length 182 which is at least about 30 percent, and alternatively is at least about 40 percent of the extent of the longitudinal length 180 of the article to provide improved effectiveness. If desired, each leg gusset section 142 can be in a bridging configuration along a length which can be up to 100 percent of the total longitudinal length of the article to provide further gasketing and containment. Alternatively, each gusset section can be in a bridging configuration along a length which is not more than about 80 percent, and optionally is not more than about 70 percent of the total longitudinal length of the article to provide desired performance and cost effectiveness.

As previously described, each gusset-flap 19 may have an overall longitudinal length which is substantially equal to the overall, total length of the article. Alternatively, each gusset-flap may have a length which is less than the overall, total length of the article, and the relatively shorter gusset-flap may be configured with a zoned-placement at a selected location along an appointed portion of the overall length of the article. Optionally, each gusset-flap 19 may have a total length which is substantially equal to or less than the overall, total length of the absorbent body structure 32, and the relatively shorter containment flap section may be configured with a zoned-placement at a selected location along an appointed portion of the overall length of the absorbent body structure.

To further control the operation of the gusset-flap 19, the arranged array of the gusset elastic members 138 and/or the arranged array of the flap elastic members 68 may be uniformly spaced across the entire width of the leg gusset section 142 and/or containment flap section 144, respectively (as determined along a dimension which is substantially perpendicular to the stretching dimension of the elastic member). Alternatively, the arrangement of the gusset elastics 138 and/or the arrangement of the flap elastics 68 may be grouped into discrete and distinct functional sets. In addition, the multiple, discrete grouping of elastics may be placed in either or both of the leg gusset or containment flap sections of the gusset-flap member 19 to control the operation of the gusset-flap and enhance its performance.

In further aspects of the invention, the elastic members in either or both of the gusset and containment flap sections 142 and 144, respectively, may be operably zone-tensioned. Desirably, the zone tensioning is configured to substantially limit the elasticized gathering to a medial, longitudinally-central section of the gusset-flap member. The zone tensioning may be achieved in a variety of ways. For example, the elastic contractility of the elastic members 138 and 68 in the appropriate end regions of the leg gusset and containment flap sections 142 and 144, respectively, can be operably deadened, such as by a mechanical, ultrasonic or thermal treatment which effectively "kills" or otherwise deactivates the elasticity or contractility in the selected regions. Alternatively, an adhesive or other bonding mechanism may be applied only in the areas where the retraction of the elastic members is intended to gather the flap composite. In the regions where the bonds are absent, the remaining elastic members can contract substantially without gathering the selected sections of the flap composite. In further configurations, the longitudinally distal end regions of the leg gusset or containment flap sections can be substantially, entirely immobilized, such as by operably securing the end regions onto the topsheet layer 28 (or other part of the article) with adhesive, sonic bonds or other attaching mechanisms.

Typically, the assembled gusset-flap 19 can be attached into the absorbent article 10 while the gusset-flap member 19 is extended to approximately the same extension that was present in the gusset-flap member when as the elastomeric members 68 and 138 were assembled and attached into the construction of the gusset-flap composite. Accordingly, the gusset-flap member may be attached and incorporated into the article while the fabric and barrier layers of the gusset-flap member are effectively fully extended to their substantially ungathered, flat-out conditions, and the elastomeric members 68 and 138 are substantially in their initially stretched conditions. Alternatively, the composite, gusset-flap member may be shirred and gathered by a selected amount of elastomeric retraction of the attached elastomeric members 68 and 138, which is allowed to occur prior to the attaching and incorporating of the composite gusset-flap member 19 into the article 10. The amount of allowed retraction and pre-gathering can be expressed in terms of a percentage based upon the initial, ungathered length of the composite gusset-flap member 19, employing the formula:

$$100*(L_i-L_f)/L_i;$$

where:

$L_i$=the initial, ungathered length of the composite gusset-flap, and $L_f$=the final, gathered length of the composite gusset-flap.

In particular aspects of the invention, the amount of allowed, prior retraction and gathering can be within the range of about 0–50%. The amount of allowed, prior retraction and gathering, in other aspects, can be at least about 10%, and in further aspects, can be not more than about 25% to provide desired benefits and performance. The selected amount of prior or pre-gathering can advantageously help to reduce the amount of gathering force that is initially transmitted to the topsheet and backsheet layers of the article during manufacture, and can help to isolate the topsheet and backsheet layers from the stretching and contracting movements of the gusset-flap member 19 which may occur while article is being worn.

With reference to FIGS. 1, 2 and 4, the pocket section 84 of the waist member 80 may be configured to bridge and span over the inward facing, bodyside surfaces of the longitudinally extending containment flap sections 144. Desirably, the movable edge portions 104 of the pocket section 84 are substantially disconnected and unattached to the distal, movable edges 66 of the containment flap sections 144 to thereby reduce interaction between the elasticized containment flap sections 144 and the elasticized pocket section 84. In addition, it can be desirable to zone the elastic tension exerted by the elastic members 68 employed to elasticize the containment flap sections 144. More particularly, the elastic tension in the containment flap sections can be substantially restricted to a longitudinally medial section of each containment flap section. Accordingly, the end regions of each containment flap section, particularly the flap end regions generally adjacent to the pocket section 84, can be substantially free of elastic tension exerted by the elastic members 68. The distal edges 66 can also be secured to the topsheet layer 28 with a suitable attaching mechanism to further isolate the distal edges 66 of the containment flap sections away from the operation and opening of the pocket section 84. Other techniques for producing the desired zoned tensioning of the containment flap sections 144 have been previously described herein.

In particular aspects of the invention, the gusset-flap members 19 can be configured to substantially avoid intersecting the locations of the waist pocket members 80. Accordingly, each of the gusset-flap members can be constructed to terminate at positions which are spaced away from the terminal edges of the pocket sections 84 of the waist pocket members. In other aspects, the gusset-flap members 19 can be configured to lay onto an inwardly facing, bodyside surface of the waist pocket members 80. The gusset-flap members 19 may then terminate in a zone starting from the gatherable moveable edge of the waist pocket 104 to the longitudinal end margin 22 of the absorbent article 10. In yet other aspects, the gusset-flap members 19 can be configured to lay underneath, adjacent an outwardly facing surface of the waist pocket members 80. The gusset-flap members 19 may then terminate in a zone starting from the gatherable moveable edge of the waist pocket 104 to the longitudinal end margin 22 of the absorbent article 10.

In the various arrangements of the invention, the selected absorbent composite system, such as a system which includes the surge management portion 46 and the absorbent body structure 32, is positioned and operably secured between the topsheet 28 and the backsheet 30 to form the diaper 10. The absorbent system has a construction which is generally compressible, conformable, non-irritating to the wearer's skin, and capable of absorbing and retaining liquid body exudates. It should be understood that, for purposes of this invention, any of components of the absorbent system may comprise a single, integral piece of material, or alternatively, may comprise a plurality of individual separate pieces of material which are operably assembled together. Where the absorbent component, such as the absorbent body 32, comprises a single, substantially integral piece of material, the material could include the desired structural features formed into selected spatial regions thereof. Where the absorbent component comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent component. Preferably, each piece is connected to an adjacent portion of the absorbent component by a suitable bonding and/or fiber entanglement mechanism, such as ultrasonic or adhesive bonding, or mechanical or hydraulic needling.

In the representatively shown embodiments, the absorbent body structure 32 has a liquid-acquisition zone, a target zone, and a contoured, curvilinear periphery, particularly along its side edges. The two generally mirror-image, inwardly bowed, lateral edges provide for a narrower intermediate section suitable for positioning in the crotch of the wearer. In the shown absorbent structure 32, a front section thereof includes two transversely spaced ear regions and a central region. The target zone encompasses the area where repeated liquid surges typically occur in absorbent structure 32. When the diaper is worn, the ear regions are configured to generally engage the sides of the wearer's waist and torso, and central region is configured to generally engage the medial portion of the wearer's waist and torso.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied. In a particular aspect of the invention, the absorbent structure has an absorbent capacity of at least about 300 gm of synthetic urine. Alternatively, the absorbent structure can have an absorbent capacity of at least about 400 gm of synthetic urine to provide improved performance.

With reference to FIG. 13, a further aspect of the article of the invention can include a distinctively configured absorbent retention portion 48. The backsheet layer 30 can have a maximum waistband width_A along the cross dimension 24 of the article, and the absorbent retention portion 48 can have a minimum width_P along the cross dimension at an intermediate portion of the retention portion 48. A quotient of the width_A divided by the width_P is at least a predetermined value, such as a minimum value of at least about 3.3. The absorbent retention portion 48 can also have a longitudinal length_Z along which a cross-directional width of the retention portion is not more than a value_Q, where the value_Q is determined by the formula, $$(\text{value\_Q}) = (0.8)*(\text{width\_P}) + (0.2)*(\text{width\_A}).$$

The length_Z is at least a selected proportion of the overall length 180 of the article. Desirably, the length_Z is at least a minimum of about 30% of an overall length 180 of the article to provide improved fit and conformance. Alternatively, the length_Z can be at least about 35% of the overall length of the article, and optionally, can be at least about 40% of the overall length of the article to provide further improved fit and leakage resistance. While the length_Z may exceed 40% of the overall length of the article, the length_Z is desirably not more than about 40% in the overall article length to allow a greater reasonable portion of the buttocks of the wearer is covered by the absorbent pad, and to provide improved appearance and aesthetics. In particular aspects, minimum cross-directional width of the retention portion at its back waistband portion is at least a minimum of about 4 inches (102 mm), but less than the width of the retention portion at its front waistband portion.

Various types of wettable, hydrophilic fibrous material can be used to form the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for the surge management portion 46 can be provided by a CAHN, SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

The retention portion 48 can comprise a matrix of hydrophilic fibers, such as a web of cellulosic fluff, mixed with particles of high-absorbency material. In particular arrangements, retention portion 48 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent structure and relatively higher concentrations toward the outerside of the absorbent structure. Suitable z-gradient configurations are described in U.S. Pat. No. 4,699,823 issued Oct. 13, 1987 to Kellenberger et al., the disclosure of which is incorporated herein by reference in a manner that is consistent with the present description. The superabsorbent particles may also be arranged in a generally discrete layer within the matrix of hydrophilic fibers or may be configured as discrete, separate pocket regions of superabsorbent material. In addition, two or more different types of superabsorbent may be selectively positioned at different locations within or along the fiber matrix.

The high-absorbency material may comprise absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in the retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in the retention portion 48.

Preferred for use are particles having an average size of from about 20 microns to about 1 millimeter. "Particle size" as used herein means the weighted average of the smallest dimension of the individual particles.

Suitable high-absorbency materials can have particular characteristics of Absorbent Capacity (sometimes referred to as "AC"), Deformation Under Load (sometimes referred to as "DUL"), and the Wicking Index (sometimes referred to as "WI"). These parameters are described in detail in U.S. patent application Ser. No. 757,787 of S. Byerly et al., entitled ABSORBENT COMPOSITES AND ABSORBENT ARTICLES CONTAINING SAME and filed on Sep. 11, 1991, the disclosure of which is hereby incorporated by reference in a manner that is consistent with the present specification.

In a particular aspect of the invention, absorbent retention portion 48 comprises a matrix of substantially hydrophilic fibers having a quantity of high-absorbency material distributed therein. Selected superabsorbent polymers having improved absorbent properties can be important for maximizing the performance while retaining the desired thinness of the absorbent article. To provide improved performance, the particles of superabsorbent material can be selected to provide an absorbency-under-load (AUL) value which is within the range of about 25–40, and provide a Absorbent Capacity (AC) value which is within the range of about 32–48. The rate of liquid uptake by the superabsorbent material is within the range of about 3–15 g/g (grams liquid per gram superabsorbent) at 30 seconds of absorbency under load, 6.5–21 g/g at 5 minutes absorbency under load and 25–40 g/g at 60 minutes absorbency under load.

A suitable method for determining AUL is described in detail in U.S. Pat. No. 5,147,343 of S. Kellenberger, granted Sep. 15, 1992 and entitled ABSORBENT PRODUCTS CONTAINING HYDROGELS WITH ABILITY TO SWELL AGAINST PRESSURE; and also published Nov. 2, 1989 as European Patent Application No. EP 0 339 461 A1; the disclosure of which is hereby incorporated by reference in a manner that is consistent with the present specification.

An example of superabsorbent polymer suitable for use in the present invention is SANWET IM 3900 polymer available from Hoechst Celanese, a business having offices in Portsmouth, Va. Other suitable superabsorbents may include DOW DRYTECH 2035LD polymer obtained from Dow Chemical Co., a business having offices in Midland, Mich.; or FAVOR SAB 870M polymer available from Stockhausen, Inc., a business having offices in Greensboro, N.C.

The matrix of hydrophilic fibers comprising retention portion 48 may be a layer of cellulosic wood pulp fluff, and the particles of superabsorbent polymer can be distributed within the matrix of hydrophilic fibers. The hydrophilic fibers and high-absorbency particles can be provided in a fiber-to-particle ratio which is not more than about 75:25, alternatively, is not more than about 70:30, and optionally, is not more than about 55:45, by weight. In further aspects of the invention, the fiber-to-particle ratio is not less than about 25:75, preferably is not less than about 30:70 and more preferably is not less than about 45:55, by weight. Such fiber-to-particle ratios can be particularly desirable in the target zone of the absorbent structure. In particular embodiments of the invention, the fiber-to-particle weight ratio is not more than about 65:35 and is not less than about 50:50 to provide desired performance.

The hydrophilic fibers and high-absorbency particles can form an average composite basis weight which is within the range of about 400–1000 gsm. Again, such basis weight is particularly desirable in the target zone of the absorbent structure. In certain aspects of the invention, the average composite basis weight is within the range of about 500–950 gsm, and preferably is within the range of about 550–900 gsm to provide desired performance.

To provide the desired thinness dimension to the various configurations of the absorbent article of the invention, retention portion 48 can be configured with a bulk thickness which is not more than about 0.6 cm. Preferably, the bulk thickness is not more than about 0.53 cm, and more preferably is not more than about 0.5 cm to provide improved benefits. The bulk thickness is determined under a restraining pressure of 0.2 psi (1.38 kPa).

The density of retention portion 48 or other component of the absorbent article can be calculated from its basis weight and thickness. With respect to diapers, for example, the weight and thickness are measured on newly unpacked, unfolded and dry diapers at a restraining pressure of 0.2 psi (1.38 kPa). Conventional thickness measuring devices may be employed to determine the thickness needed to calculate the density.

In the illustrated embodiments of the invention, absorbent retention portion 48 can include 4–30 grams of wood pulp fluff, preferably includes about 8–18 grams of fluff and more preferably includes about 12–14 grams of fluff to provide desired benefits. The wood pulp fluff generally provides shape and form to diaper 10, and carries and positions the particles of superabsorbent polymer or other high-absorbency material. The retention portion 48 can contain about 5–20 grams of superabsorbent polymer, and in the shown embodiment, contains about 8 grams of superabsorbent polymer. Sufficient superabsorbent polymer is incorporated into retention portion 48 to provide an adequate total absorbent capacity of at least about 300 gm of synthetic urine. For example, a medium size diaper for an infant weighing about 16–28 lb (about 7–13 kg) can typically have a total retention capacity of about 400 grams of synthetic urine.

The fluff and superabsorbent particles can be selectively placed into desired zones of retention portion 48. For example, the fluff basis weight may vary across the width dimension of retention portion 48. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material may be distributed down a medial region of retention portion 48 which extends along the length dimension of the retention portion and measures about 1–4.5 inches (about 2.5–11.4 cm) in width. In addition, the superabsorbent material may have a selected zoned placement to reduce the amount of superabsorbent material located proximate the side and end edges of the retention portion. The reduced amounts of superabsorbent material at the edges of the retention portion can improve the containment of the superabsorbent particles within the fibrous fluff matrix of retention portion 48. The pulsed, zoned placement of the superabsorbent material can, for example, be achieved by the method and apparatus described in U.S. Pat. No. 5,028,224 to C. Pieper et al., entitled METHOD AND APPARATUS FOR INTERMITTENTLY DEPOSITING PARTICULATE MATERIAL IN A SUBSTRATE and issued Jul. 2, 1991, the disclosure of which is hereby in corporated by reference in a manner that is consistent herewith.

In a desired configuration of the invention, the absorbent structure 32, particularly the retention portion 48, can be generally T-shaped with the laterally extending cross-bar of the "T" generally corresponding to the front waistband portion of the absorbent article for improved performance, especially for male infants. In the illustrated embodiments, for example, the retention portion across the ear section of the front waistband region of the article has a cross-directional width of about 7.25 inches (about 18.4 cm), the narrowest portion of the crotch section has a width of about 2.6 inches (about 6.6 cm) and the back waistband region has a width of about 5.6 inches (about 14.2 cm).

The entire absorbent structure 32, or any individual portion thereof, such as the retention portion 48, can be overwrapped in a hydrophilic high wet-strength envelope web, such as a high wet-strength tissue or a synthetic fibrous web. Such overwrapping web can also increase the in-use integrity of the absorbent structure. The web can be suitably bonded, such as with adhesive, to absorbent structure 32 and to other components of the product construction.

Due to the high concentrations of superabsorbent particles, or other high-absorbency material, in the retention portion 48, there can be an increased difficulty with regard to containing the high-absorbency particles within the retention portion and restricting the movement or migration of the superabsorbent onto the bodyside of the diaper. To improve the containment of the high-absorbency material, absorbent structure 32 can include an improved overwrap, such as a wrap sheet 70, placed immediately adjacent and around retention portion 48. The wrap sheet is preferably a layer of absorbent material which covers the major bodyside and outerside surfaces of the retention portion, and preferably encloses substantially all of the peripheral edges of the retention portion to form a substantially complete envelope thereabout. Alternatively, the wrap sheet can provide an absorbent wrap which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the retention portion at the waistband regions of the article.

Absorbent wrap 70 may comprise a multi-element wrap-sheet which includes a separate bodyside wrap layer and a separate outerside wrap layer, each of which extends past all or some of the peripheral edges of retention portion 48, as representatively shown in FIG. 1. Such a configuration of the wrap sheet can, for example, facilitate the formation of a substantially complete sealing and closure around the peripheral edges of retention portion 48. In the back waistband portion of the illustrated diaper, the absorbent wrap may also be configured to extend an increased distance away from the periphery of the retention portion to add opacity and strength to the back ear sections of the diaper. In the illustrated embodiment, for example, the bodyside and outerside layers of absorbent wrap 70 extend at least about ½ inch (about 1.3 cm) beyond the peripheral edges of the retention portion to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 70 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs and facilitate the processibility of the absorbent pad. To provide the bonding between the bodyside and outerside portions of absorbent wrap 70, an adhesive, such as NATIONAL STARCH 72-3723 adhesive, can be printed onto the appointed bonding areas of the absorbent wrap with, for example, a rotogravure-type system. With alternative arrangements having an absorbent wrap composed of a nonwoven meltblown fibrous web, the peripheral sealing of the bodyside and outerside wrap layers may be accomplished by employing hot calendering to provide a sealed strip region around the periphery of the retention portion.

Due to the thinness of retention portion 48 and the high superabsorbent concentrations within the retention portion, the liquid uptake rates of the retention portion, by itself, may be too low, or may not be adequately sustained over multiple insults of liquid into the absorbent structure. The addition of a porous, liquid-permeable layer of surge management material, however, can advantageously improve the overall uptake rate of the composite absorbent structure. Surge management portion 46 is typically less hydrophilic than retention portion 48, and has an operable level of density and basis weight to quickly collect and temporarily hold liquid surges, to transport the liquid from its initial entrance point and to substantially completely release the liquid to other parts of the absorbent structure 32, particularly retention portion 48. This configuration can help prevent the liquid from pooling and collecting on the portion of the absorbent garment positioned against the wearer's skin, thereby reducing the feeling of wetness by the wearer.

Various woven and nonwoven fabrics can be used to construct surge management portion 46. For example, the surge management portion may be a layer composed of a meltblown or spunbonded web of polyolefin fibers. The surge management layer may also be a bonded-carded-web or an airlaid web composed of natural and synthetic fibers. The bonded-carded-web may, for example, be a powder-bonded-carded web, an infrared bonded carded web, or a through-air-bonded-carded web. The infrared and through-air bonded carded webs can optionally include a mixture of different fibers, and the fiber lengths within a selected fabric web may be within the range of about 1.0–3.0 inch. The surge management portion may be composed of a substantially hydrophobic material, and the hydrophobic material may optionally be treated with a surfactant or otherwise processed to impart a desired level of wettability and hydrophilicity.

The representative diaper 10 can include a surge management portion 46 which is arranged in a direct, contacting liquid communication with an adjacent absorbent retention portion 48. As representatively shown, surge management portion 46 may be configured for placement adjacent an outwardly facing, outerside of topsheet 28. Optionally, the surge management portion can be placed adjacent an inwardly facing, bodyside surface of topsheet layer 28. The shown configuration of the surge management portion is operably connected to the topsheet layer with a conventional pattern of adhesive, such as a swirl adhesive pattern. In addition, the surge management portion can be operably connected to the bodyside layer of wrapsheet 70 with a conventional pattern of adhesive. The amount of adhesive add-on should be sufficient to provide the desired levels of bonding, but should be low enough to avoid excessively restricting the movement of liquid from the topsheet layer, through the surge management portion and through the wrapsheet layer.

The retention portion 48 is positioned in liquid communication with surge management portion 46 to receive liquids released from the surge management portion, and to hold and store the liquid. In the shown embodiments, surge management portion 46 comprises a separate layer which is positioned over another, separate layer comprising the retention portion, thereby forming a dual-layer arrangement. The surge management portion serves to quickly collect and temporarily hold discharged liquids, to transport such liquids from the point of initial contact and spread the liquid to other parts of the surge management portion, and then to substantially completely release such liquids into the layer or layers comprising retention portion 48.

The representatively shown configuration of the surge management portion is substantially free of absorbent gelling material. Surge management portion 46 may, however, contain a very small amount of particulate gelling material to help acquire an initial liquid surge, but the amount should not be excessive. When excessive amounts of particulate absorbent gelling material are maintained in the target zone, however, the particles can cause the structure to retain and hold unacceptably high amounts of the liquid. In addition, the transport of liquids away from the target zone to other sections of absorbent structure 32, particularly retention portion 48, can be undesirably impaired.

As mentioned previously, the surge management portion 46 can be a separately formed layer, which lies adjacent the outwardly facing surface of topsheet 28 between the retention portion and topsheet. Thus, surge management portion 46 need not comprise the entire thickness of absorbent structure 32. The retention portion can optionally include a recess area which wholly or partially surrounds surge management portion 46, or the retention portion can be entirely positioned below the surge management portion. The arrangement which includes the recess in the retention portion 48 can advantageously increase the area of contact and liquid communication between the retention portion and surge management portion 48. It should be understood, however, that surge management portion 46 could optionally be constructed to extend through the entire thickness of absorbent structure 32 so that the capillary flow of liquid into retention portion 48 occurs primarily in a generally sideways (X-Y) direction.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized. In certain embodiments, for example, the surge management portion can be generally rectangular-shaped.

In the various configurations of the invention, surge management portion 46 may extend over the complete length of retention portion 48, or may extend over only a part of the retention portion length. Where the surge management portion extends only partially along the length of the retention portion, the surge management portion may be selectively positioned anywhere along absorbent structure 32. For example, surge management portion 46 may function more efficiently when it is offset toward the front waistband of the garment and transversely centered within a front section of absorbent structure 32. Thus, surge management portion 46 can be approximately centered about the longitudinal center line of absorbent structure 32, and positioned primarily in a central region of a front section of the absorbent structure 32.

In other aspects of the invention, the end edges of the surge management portion can be spaced longitudinally inboard from the end edges of the retention portion 48. In particular configurations of the invention, the corresponding, relatively adjacent front end edge of surge management portion 46 can be spaced a predetermined discrete distance from a front waistband end edge of the retention portion 48.

It has been found that an effective fabric for constructing the surge management portion can be distinctively characterized by particular parameters. Such parameters include, for example, basis weight, permeability, porosity, surface area per void volume (SA/VV), compression resiliency and saturation capacity. Further parameters can include a bonding matrix which will help stabilize the pore size structure, and hydrophilicity. The bond-matrix and the blend of fiber deniers can advantageously provide for and substantially maintain a desired pore size structure.

Additional details regarding the surge materials and suitable techniques for determining the above-described parameters are set forth in U.S. Pat. No. 5,486,166 issued Jan. 23, 1996 to C. Ellis et al., entitled FIBROUS NONWOVEN WEB SURGE LAYER FOR PERSONAL CARE ABSORBENT ARTICLES AND THE LIKE; and U.S. Pat. No. 5,490,846 granted Feb. 13, 1996 to C. Ellis et al., entitled IMPROVED SURGE MANAGEMENT FIBROUS NONWOVEN WEB FOR PERSONAL CARE ABSORBENT ARTICLES AND THE LIKE; the disclosures of which are hereby incorporated by reference in a manner that is consistent herewith.

Alternatively, the surge management portion 46 can include two (or more) separate plies of material which are bonded or otherwise integrated together and then incorporated in the absorbent article. A top ply can be designed to have a more open structure than a bottom ply, and the layered surge management portion can be placed in the article with the top ply towards the topsheet 28 and the bottom ply towards the absorbent core 32. The bottom ply may also have fibers with higher amounts of fiber orientation than the top ply. The fibers can be aligned so that liquid is more likely to spread in the longitudinal direction of the article. In this manner, the top ply can provide a layer configured for liquid intake while the bottom ply provides a layer configured for liquid spreading prior to absorption by the absorbent core. Optionally, a majority of the fibers in the bottom ply may be either less hydrophilic or of substantially equal hydrophilicity as compared to a majority of the fibers of the top ply. The majority fiber in the ply is defined as the fiber component with the highest weight of fiber in the ply.

The top ply of the layered surge management portion 46 can have a basis weight within the range of about 1.0 to 3.5 osy (about 34 to 119 g/m$^2$), and can have a fabric density within the range of about 0.010–0.045 g/cm$^3$. The fibers consist of a mix of natural or synthetic fibers manufactured in such a way to provide a structure having a calculated permeability of about 1000–4000 square microns, as calculated by a Riese permeability model. The Riese permeability model is described in detail in U.S. patent application Ser. No. 556,678 filed Nov. 13, 1995, and entitled LOFTY NONWOVEN FABRIC by C. Ellis et al., the entire disclosure of which is incorporated by reference in a manner that is consistent herewith.

The bottom ply of the layered surge management portion 46 can have a basis weight within the range of about 0.5 to 2.5 osy (about 17 to 85 g/m$^2$) and can have a fabric density within the range of about 0.040–0.060 g/cm$^3$. The bottom ply can also have a density higher than the top ply density. The fibers can include a mix of natural or synthetic fibers manufactured in such a way to provide a structure having a calculated permeability of about 100–1000 square microns, as calculated by the Riese permeability model.

An example of a surge management fabric with two plies described by the parameters above would be a thermally bonded carded web made on a carding line with multiple cards. The top layer can include 60% bicomponent fiber, and 40% 6 denier polyester (PET) fiber. The top layer blend is carded into a "random" fiber orientation of about 3:1 machine direction/cross direction (MD/CD) ratio. In the top layer, the bicomponent may be either a 2 or 3 denier fiber of the core/shell type, with polyethylene as the primary component of the shell portion of the fiber. Examples of these bicomponent fibers include Chisso ESC-HR6 or Hoechst Celanese (or Hoechst Trevira) T256. An example of the PET fiber is T295 from Hoechst Celanese (or Hoechst Trevira). The bottom layer can include a 100% bicomponent fiber which is carded into a high MD orientation of about 12:1. In the bottom layer, the bicomponent fiber may be either a 2 or 3 denier fiber of the core/shell type, with polyethylene as the primary component of the shell portion of the fiber. Examples of these bicomponent fibers would be Chisso ESC-HR6 or Hoechst Celanese (Hoechst Trevira) T256.

Various surge management portions which include fabrics composed of multiple plies or layer regions are further described in U.S. patent application Ser. No. 754,417 filed Nov. 22, 1996 and entitled HETEROGENEOUS SURGE MATERIAL FOR ABSORBENT ARTICLES by R. Dodge et al, the entire disclosure of which is incorporated by reference in a manner that is consistent herewith.

In desired configurations of the invention, the surge material can include natural fibers, synthetic fibers, such as synthetic polymer fibers, and combinations thereof. The fabric can, for example, be composed of polyolefin fibers, and in particular configurations the fibers can include bicomponent fibers. For example, polypropylene/polyethylene bicomponent fibers may be employed to form the bicomponent fiber portion of any of the described fabrics. In addition, the bicomponent fibers may be flat crimped or helically crimped.

In the shown configuration of the article, the side panel members 56 are separately provided members which are operably connected and attached to laterally opposed end sections of the back waistband portion of backsheet 30. In particular, each side panel is affixed to extend away from a corresponding terminal edge of the backsheet layer. The side panels can be composed of a substantially non-elastomeric material, such as polymer films, woven fabrics, nonwoven fabrics or the like, as well as combinations thereof. In particular aspects of the invention, the side panels are composed of an elasticized material, such as a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. No. 4,663,220 issued May 5, 1987 to T. Wisneski et al., the disclosure of which is hereby incorporated by reference. Examples of composite fabrics comprising at least one layer of nonwoven textile fabric secured to a fibrous elastic layer are described in European patent application No. EP 0 110 010 published on Apr. 8, 1987 as EP 0 217 032 A2 with the inventors listed as J. Taylor et al., the disclosure of which is hereby incorporated by reference. Examples of NBL materials are described in U.S. Pat. No. 5,226,992 issued Jul. 13, 1993 to M. Mormon, the disclosure of which is hereby incorporated by reference.

Examples of articles which include elasticized side panels and selectively configured fastener tabs are described in U.S. patent application Ser. No. 168,615 of T. Roessler et al., entitled DYNAMIC FITTING DIAPER, and filed Dec. 16, 1993. Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995; in U.S. Pat. No. 5,540,796 which issued Jul. 30, 1996 to D. Fries, entitled A PROCESS FOR ASSEMBLING ELASTICIZED EAR PORTIONS; in U.S. Pat. No. 5,595,618 which issued Jan. 21, 1997 to D. Fries, entitled AN ASSEMBLY PROCESS FOR A LAMINATED TAPE; and in U.S. Pat. No. 5,549,592 which issued Aug. 27, 1996 to D. Fries, entitled AN ABSORBENT ARTICLE WITH A LAMINATED TAPE. The entireties of the disclosures of the above-described documents are incorporated herein by reference in a manner that is consistent (not in conflict) herewith.

The fastener system can optionally include a separately provided reinforcement strip which is composed of a strengthening and/or stiffening material, and is laminated to an appointed first surface of each of the side panel members 56 at the outboard region of the side panel. The shown reinforcement strip extends along substantially the entire length of the outboard end portion of the panel member 56. In addition, the reinforcement strip has a length which is greater than the length dimension of the securing mechanism 44 on the user-bond portion 38 of the fastener tab 36. The reinforcement strip can, for example, be composed of a release tape, and the release tape can include a substrate composed of a polymer film, such as a polypropylene film. Suitable release tape materials are available from Avery Corp., a business having offices located in Painesville, Ohio.

In particular, the reinforcement strip can be operably bonded and laminated to the outboard region of the panel member 56 along the first surface of the panel member. The shown reinforcement strip can be configured with its terminal outboard edge positioned substantially coterminous and substantially coextensive with the outboard edge of the panel member 56. In addition, the width of the release tape along the cross-direction 24 is desirably equal to or greater than the width of the securing mechanism 44 provided on the user-bond region 38 of the fastener tab 36.

The illustrated fastening system includes a complementary, opposed pair of fastener tabs 36, which provide a mechanism for holding the article on the wearer. Each of the fastener tabs includes a tab substrate 86, which may be composed of various substrate materials. For example, the shown embodiment of the tab substrate can be composed of a polymer film, such as a polypropylene film. Suitable film materials are available from Avery Corp., a business having offices located in Painesville, Ohio. Alternatively, the securement web may include a woven or nonwoven fabric, such as spunbond nonwoven fabric.

The representatively shown tab substrate 86 includes an appointed securement surface and an opposed user surface, and includes a selected securing means which is positioned onto the securement surface of the tab substrate. The securing means may be provided by an adhesive, a cohesive material, a cooperating component of a interengaging, mechanical fastener, snaps, pins or buckles and the like, as well as combinations thereof. For example, the securing means may include a hook (e.g. mushroom-head) component or a loop component of a hook-and-loop fastener. In the shown configuration, the securing means is provided by a layer of primary adhesive distributed over the appointed securing surface, and the fastening system provides an adhesive fastener tab. The fastener tabs can be constructed to releasably adhere to an appointed landing zone patch 92 which is attached to the front waistband section of the diaper to provide an adhesive or mechanical fastening system which is refastenable.

With the adhesive securing means, the layer of primary adhesive can be employed to operably laminate and affix the appointed factory-bond region 39 of the fastener tab 36 to the outboard region of the panel member 56 along an appointed second surface of the panel member. Other types of connecting means, such as thermal bonds, sonic bonds, mechanical stitching, stapling and the like, as well as combinations thereof, may alternatively be employed to permanently attach the fastener tab to the panel member. For example, ultrasonic bonds may be employed to provide a selected supplemental bonding.

With reference to FIG. 1, the fastener tab 36 includes a factory-bond section 39 which overlaps the outboard edge of the panel member 56, and extends beyond the panel member to provide the user-bond region of the fastener tab. In particular arrangements of the invention, the fastener tab can have a relatively wide user-bond section in combination with a relatively narrower intermediate section. The intermediate section is positioned between the user-bond and factory-bond sections of the fastener tab. In a further aspect of the invention, the fastener tab 36 may optionally include a finger tab region. The finger tab can be substantially non-securing, and can provide an area that can be readily grasped by the user without contaminating or otherwise adversely affecting the securing means.

Various types and arrangements of interengaging mechanical securing means can be employed to provide an operable fastening system for the various configurations of the invention. Representative examples of suitable mechanical fastener configurations are described in U.S. Pat. No. 5,605,735 which issued Feb. 25, 1997 to G. Zehner et al., entitled HIGH-PEEL TAB FASTENER; and in U.S. patent application Ser. No. 421,640 by P. VanGompel et al., entitled MULTI-ATTACHMENT FASTENING SYSTEM and filed Apr. 13, 1995, the entire disclosures of which are hereby incorporated by reference in a manner that is consistent herewith.

EXAMPLE

The following example is presented to provide a more detailed understanding of the invention. The example is representative, and is not intended to limit the scope of the invention.

A representative example of the invention provided a "size 4" or "medium" diaper for an infant weighting between 16–28 pounds. The diaper included a shaped absorbent pad 32 composed of superabsorbent and wood fluff pulp. The absorbent was formed and wrapped with high wet-strength, kraft tissue wrapsheet 70 on at least the topsheet side of the absorbent pad 32. A tissue cutout was then used to shape the tissue to have a slightly larger lateral dimension but roughly the same shape as the absorbent pad. The surge management layer 46 was composed of a through-air bonded carded web with a basis weight of about 3.5 osy and a density of about 0.024 g/cm$^3$. The surge management layer was adhesively attached to the topsheet 28, which was composed of a surfactant treated spunbond fabric. Separately, the fastener landing zone patch 92 was laminated at the front waistband portion of the backsheet layer 30, and the backsheet layer was composed of a clothlike, polymer film and nonwoven fabric laminate. The assembly of the surge management portion 46 and the topsheet layer 28 was then combined with the absorbent pad 32, the tissue wrap 70, and the landing zone 92/backsheet 30 combination. The topsheet layer 28 and backsheet layer 30 were then cut to form the side edge contours 15 of the diaper. Fasteners 36 were then attached near the lateral edges of the back waistband portion on the surface of the topsheet layer.

A pair of gusset-flaps were formed with each gusset-flap employing its corresponding flap elastomeric members 68, leg gusset elastomeric members 138, gusset-flap barrier layer 134, and gusset-flap fabric layer 176. The containment flap and leg gusset elastomeric members 68 and 138 were composed of SPANDEX elastomeric strands sized to give the desired tensions in the containment flap and leg gusset sections of the gusset-flap. The gusset-flap barrier layer 134 was composed of a cast embossed, multilayered film, while the gusset-flap fabric layer 176 was composed of a spunbond fabric material. The containment flap elastomeric members 68 and the leg gusset elastomeric members 138 were sprayed with a hot melt adhesive to substantially coat the elastomeric members with adhesive. In each gusset-flap member 19, the coated elastomeric members were then laminated with the barrier layer 134 and with the fabric layer 176 in set arrangements, and the fabric layer 134 was then folded on itself along a pair of generally parallel fold lines to form the gusset-flap member. After the folding of the gusset-flap fabric layer, ultrasonic bonds were employed to provide fabric edge securements 126 with a longitudinally extending bonding pattern which secured the terminal edge of the folded-over fabric layer 176 in the containment flap section 144 to the gusset-flap structure. The elastomeric members at the end regions of each gusset-flap 19 were then deactivated using an ultrasonic cutting device to form the containment flap distal deadening array 78 and the leg gusset distal deadening array 158.

A bead adhesive was then applied to each gusset-flap member 19 to form the gusset-flap attachment 172. Additional adhesive, in an arrangement pattern which roughly matched the width of the containment flap section and the leg gusset section, was applied to the ends of each gusset-flap to attach the end portions of the gusset-flap 19 to the article. The longitudinal length-wise extent of the containment flap end adhesive was about 50 mm at both the front and back waistband portions of the article. The longitudinal length-wise extent of the leg gusset end adhesive was about 60 mm in the article front waistband portion, and was about 85 mm in the article back waistband portion. It should be readily appreciated that the longitudinal length of the adhesive pattern employed to attach for the end portions of containment flap section and the end portions of the gusset-flap section may be varied at either or both longitudinal ends of the article. The gusset-flap member 19 was then attached to the article near the lateral side edges of the product.

After the gusset-flap 19 was applied to the article, the perimeter bonds 130 and the leg gusset outboard securements 160 were then applied to the absorbent article using an ultrasonic bonding apparatus to further attach the gusset-flap 19 to the article. The waistband pocket member 80, which is a laminate made from spunbond fabric, SPANDEX elastomeric strands, and polyolefin film, was then attached to the article with a hot melt adhesive.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An absorbent article having a longitudinal direction, a lateral cross dimension, a front waistband portion, a back waistband portion, an intermediate portion which interconnects said front and back waistband portions, and a pair of laterally opposed and longitudinally extending side margins, each side margin having an outwardly concave, terminal side edge contour located at an appointed leg opening region in an intermediate portion of said each side margin, each concave side edge contour having a selected longitudinal extent along said length dimension of said article, said article comprising:

a backsheet layer having an outward surface and an opposed, inward bodyside surface;

a substantially liquid permeable topsheet layer superposed over said bodyside surface of said backsheet layer;

an absorbent body sandwiched between said topsheet layer and said backsheet layer;

a separately provided gusset-flap composite member connected to said article along each of said leg opening regions, said gusset-flap member providing a leg gusset section and a containment flap section, wherein each leg gusset section is configured to extend laterally beyond and bridge across at least a portion of its corresponding outwardly concave terminal side edge contour of said backsheet layer, and each leg gusset section is configured to elasticize its corresponding leg opening region of said article, each containment flap section is integrally formed with a corresponding one of said leg gusset sections and positioned relatively inboard therefrom to provide an inner barrier flap, each containment flap section has a longitudinally extending, substantially fixed edge portion located proximally adjacent to a one of said elasticized leg openings, and has an elasticized distal edge portion, with at least an intermediate portion of said distal edge portion being movable to a position spaced away from said article, a first arrangement of a first plurality of separate, longitudinally extending elastomeric members are attached within said leg gusset section of each said gusset-flap member, and a second arrangement of at least one longitudinally extending elastomeric member are attached within said containment flap section of each said gusset-flap member;

a gusset-flap attachment which has a longitudinal extent and secures each said gusset-flap member to said article along said fixed edge portion of each containment flap section; and an additional perimeter bond attachment which is positioned adjacent to and laterally outboard from each said gusset-flap attachment, each article edge attachment configured to secure its associated leg gusset section to said article beside its corresponding, outwardly concave terminal side edge contour of said article along at least a partial length of said terminal side edge contour, wherein said perimeter bond attachment is located along a perimeter bond attachment line which extends inboard from a terminal side edge of said backsheet layer adjacent an article juncture region where an overlapping portion of the outboard edge of at least one said leg gusset section intersects across said terminal side edge contour and said overlapping portion of the outboard edge of said at least one leg gusset section is superposed over said bodyside surface of said backsheet layer.

2. The article as recited in claim 1, wherein said additional perimeter bond attachment provides a seal against leakage of liquid between the gusset-flap member and topsheet, and between topsheet and backsheet along at least a significant longitudinal length of said intermediate portion of said article.

3. The article as recited in claim 1, wherein said additional perimeter bond attachment allows said leg gusset section to act substantially independently from said backsheet and topsheet layers at said article juncture region where a one of said waistband portions transitions into said intermediate portion of the article, and where the overlapping portion of the outboard edge of the leg gusset section is superposed with at least said backsheet layer, to thereby provide better conformance of the leg gusset to the body.

4. The article as recited in claim 1, wherein an outboard edge of said leg gusset section is substantially unattached to said article along a free-edge length of at least about 16 cm.

5. The article as recited in claim 1, wherein an outboard edge of said leg gusset section is unattached to said article along a free-edge length which is at least about 44% of an overall length of said article.

6. The article as recited in claim 1, wherein a perimeter bond spacing distance between said perimeter bond attachment and said an outboard edge of the leg gusset section is at least about 15 mm, with respect to a substantially continuous, longitudinal article distance of at least about 20% of an overall article length.

7. An absorbent article as recited in claim 1, wherein:
each said gusset-flap member includes
a barrier layer having a pair of laterally opposed, longitudinally extending, barrier layer side edges, and first and second major facing surfaces,
a fabric layer which is joined in facing relation with said first facing surface of said barrier layer, said fabric layer having a leg gusset region and a containment flap region,
said first arrangement of said first plurality of separate, longitudinally extending elastomeric members are attached to and sandwiched by said barrier layer and said fabric layer within said leg gusset section of said gusset-flap member, and
said second arrangement of at least one longitudinally extending elastomeric member is attached to at least said fabric layer within each containment flap section of said gusset-flap member.

8. An article as recited in claim 7, wherein said barrier layer includes a breathable spunbond-meltblown fabric.

9. An article as recited in claim 8, wherein said barrier layer includes a breathable spunbond-meltblown-spunbond fabric.

10. An article as recited in claim 7, wherein said barrier layer includes a breathable film.

11. An article as recited in claim 7, wherein said barrier layer includes an outboard side portion and an inboard side portion, said outboard side portion arranged to wrap around at least one side edge of said barrier layer and extend inboard therefrom along said second facing surface of said barrier layer.

12. An article as recited in claim 1, wherein each said leg gusset section is substantially liquid impermeable.

13. An article as recited in claim 1, wherein
said backsheet layer has a maximum waistband width_A along said cross dimension, and has a minimum crotch width_B at an intermediate portion of said backsheet layer;
a quotient of said maximum waistband width_A divided by said minimum crotch width_B of said backsheet layer is at least about 1.6;
said backsheet layer has a length_K along which a cross-directional width of said backsheet is not more than a value_C, said value_C determined by the formula, $$(value\_C)=(0.8)*(width\_B)+(0.2)*(width\_A);$$

said length_K is at least about 30% of an overall length of said article; and
said backsheet layer has a front turn-out angle_$\theta$ which is within the range of about 115–135 degrees.

14. An article as recited in claim 13, wherein:
said absorbent retention portion has a minimum width_P along said cross-direction at an intermediate portion of said retention portion;
a quotient of said width_A divided by said width_P is at least a minimum of about 3.3;
said absorbent retention portion has a longitudinal length_Z along which a cross-directional width of said retention portion is not more than a value_Q, said value_Q is determined by the formula, $$(value\_Q)=(0.8)*(width\_P)+(0.2)*(width\_A); and$$

said length_Z is at least about 30% of an overall length of said article.

15. An article as recited in claim 1, wherein said article further comprises a leg gusset, outboard securement which attaches an outboard side edge of at least one gusset end portion of each leg gusset section to the article.

16. An article as recited in claim 13, wherein said first arrangement of elastomeric members in said leg gusset section has an effective free elastic length of at least about 44% of a total length of said article.

17. An absorbent article having a longitudinal length dimension, a lateral cross dimension, a front waistband portion, a back waistband portion, an intermediate portion which interconnects said front and back waistband portions, and a pair of laterally opposed and longitudinally extending side margins, each side margin having an outwardly concave, terminal side edge contour located at appointed leg opening regions in the intermediate portion of said each side margin, each concave side edge contour having a selected longitudinal extent along said length dimension of said article, said article comprising:
a backsheet layer;
a substantially liquid permeable topsheet layer connected in a superposed facing relation to said backsheet layer;
an absorbent body sandwiched between said topsheet layer and said backsheet layer;

a separately provided gusset-flap composite member joined to said article along each of said leg opening regions, said gusset-flap member providing a leg gusset section and a containment flap section; wherein each leg gusset section is configured to extend beyond and bridge across its corresponding, outwardly concave terminal side edge contour of said backsheet layer to provide an elasticized leg opening region of said article;

each leg gusset section has longitudinally opposed, gusset end portions, a gusset intermediate portion located between said gusset end portions, and has a longitudinally extending, outboard distal edge portion, each containment flap section is integrally formed with a corresponding one of said leg gusset sections and positioned relatively inboard therefrom to provide an inner barrier flap;

each containment flap section has longitudinally opposed, flap end portions, a flap intermediate portion located between said flap end portions, a substantially fixed edge which extends longitudinally and is located proximally adjacent to a one of said elasticized leg openings, and has a longitudinally extending distal edge portion, at least an intermediate portion of said distal edge portion being movable to a position spaced away from said article;

a first arrangement of a first plurality of separate, longitudinally extending elastomeric members are attached within said leg gusset section of said gusset-flap member, and a second arrangement of at least one longitudinally extending elastomeric member are attached within each containment flap section of said gusset-flap member;

a gusset-flap attachment which has a longitudinal extent and secures each said gusset-flap member to said article along said substantially fixed edge of each said containment flap section; and a leg gusset, outboard deadening array which deactivates an end portion of said first arrangement of elastomeric members to provide at least one gusset end portion of each leg gusset section which is substantially non-gathered.

18. An article as recited in claim 17, wherein said end portion of said first arrangement of elastomeric members is deactivated at a plurality of longitudinally spaced apart locations to provide the at least one gusset end portion of each leg gusset section which is substantially non-gathered.

19. An article as recited in claim 17, wherein said end portion of said first arrangement of elastomeric members is segmented at a plurality of longitudinally spaced apart locations to provide the at least one gusset end portion of each leg gusset section which is substantially non-gathered.

20. An article as recited in claim 17, wherein said leg gusset outboard deadening array provides a segmenting of said end portion of said first arrangement of elastomeric members at a first plurality of longitudinally spaced apart locations to provide the at least one gusset end portion of each leg gusset section which is substantially non-gathered.

21. An article as recited in claim 17, wherein at least one end portion of said second arrangement of at least one elastomeric member is deactivated to provide at least one substantially non-gathered, flap end portion of each containment flap section.

22. An article as recited in claim 17, wherein, an end portion of said second arrangement of at least one elastomeric member is deactivated at a second plurality of longitudinally spaced apart locations to provide the at least one substantially non-gathered, flap end portion of each containment flap section.

23. An article as recited in claim 17, wherein said article further comprises a containment flap, distal securement which attaches at least one flap end portion of each containment flap section to said article.

24. An article as recited in claim 17, wherein said containment flap, distal securement attaches said leg gusset to said article at a second plurality of longitudinally spaced apart locations, and said end portion of said second arrangement of elastomeric members is segmented at said second plurality of longitudinally spaced apart locations to provide the at least one substantially non-gathered, flap end portion of each containment flap section.

25. An article as recited in claim 17, wherein said article further comprises a leg gusset, outboard securement which attaches an outboard side edge of at least one gusset end portion of each leg gusset section to the article.

* * * * *